United States Patent
Bluechel et al.

(10) Patent No.: US 12,290,621 B2
(45) Date of Patent: May 6, 2025

(54) DIALYSATE REGENERATOR COMPRISING REVERSIBLE RETAINER

(71) Applicant: TEMASEK POLYTECHNIC, Singapore (SG)

(72) Inventors: Christian Gert Bluechel, Singapore (SG); Cathy Padua Sagun, Singapore (SG); Puay Meng Tang, Singapore (SG); Liutong Lin, I, Singapore (SG); Hua Zhang, Singapore (SG); Keng Hong Lee, Singapore (SG)

(73) Assignee: TEMASEK POLYTECHNIC, Singapore (SG)

( * ) Notice: Subject to any disclaimer, the term of this patent is extended or adjusted under 35 U.S.C. 154(b) by 236 days.

(21) Appl. No.: 17/918,818

(22) PCT Filed: Apr. 13, 2021

(86) PCT No.: PCT/SG2021/050208
§ 371 (c)(1),
(2) Date: Oct. 13, 2022

(87) PCT Pub. No.: WO2021/211060
PCT Pub. Date: Oct. 21, 2021

(65) Prior Publication Data
US 2024/0058514 A1     Feb. 22, 2024

(30) Foreign Application Priority Data

Apr. 13, 2020 (SG) ........................... 10202003361W
Apr. 13, 2020 (SG) ........................... 10202003363P
Apr. 13, 2020 (SG) ........................... 10202003365X

(51) Int. Cl.
*A61M 1/16* (2006.01)
*A61M 1/14* (2006.01)
(Continued)

(52) U.S. Cl.
CPC ........ *A61M 1/1696* (2013.01); *A61M 1/1563* (2022.05); *A61M 1/1603* (2014.02);
(Continued)

(58) Field of Classification Search
CPC .............. A61M 1/1563; A61M 1/1603; A61M 1/1605; A61M 1/1607; A61M 1/1609;
(Continued)

(56) References Cited

U.S. PATENT DOCUMENTS 7,241,272 B2    7/2007  Karoor et al.
2010/0078387 A1    4/2010  Wong
(Continued)

FOREIGN PATENT DOCUMENTS

WO    WO 2002/043859 A2    6/2002
WO    WO 2007/103411 A1    9/2007
WO    WO 2009/157877 A1    12/2009

OTHER PUBLICATIONS

Association for the Advancement of Medical Instrumentation (AAMI) Technical Information Report:77, 2018 *Sorbent-based regenerative hemodialysis systems*, (31 pages).
(Continued)

*Primary Examiner* — Dirk R Bass
(74) *Attorney, Agent, or Firm* — VIERING, JENTSCHURA & PARTNER mbB

(57) ABSTRACT

An aspect of the disclosure relates to a dialysate regenerator, including: a purification means; at least one reversible retainer including an ion reservoir; a dialysate flow path including a dialysate inlet for receiving a dialysate, a dialysate outlet for dispensing the dialysate, the purification means and the at least one reversible retainer: a pump connected to the dialysate flow path and configured to generate a flow of the dialysate from the dialysate inlet via the reversible retainer and the purification means to the
(Continued)

dialysate outlet, wherein a direction of the dialysate flow path through the reversible retainer is reversible.

19 Claims, 27 Drawing Sheets

(51) Int. Cl.

| | |
|---|---|
| *A61M 1/26* | (2006.01) |
| *B01D 15/16* | (2006.01) |
| *B01D 15/18* | (2006.01) |
| *B01D 15/36* | (2006.01) |
| *B01J 20/20* | (2006.01) |
| *B01J 20/28* | (2006.01) |
| *B01J 39/02* | (2006.01) |
| *B01J 39/10* | (2006.01) |
| *B01J 39/12* | (2006.01) |
| *B01J 41/02* | (2006.01) |
| *B01J 41/10* | (2006.01) |
| *B01J 47/018* | (2017.01) |
| *B01J 47/024* | (2017.01) |
| *B01J 47/026* | (2017.01) |
| *B01J 47/12* | (2017.01) |

(52) U.S. Cl.
CPC .......... *A61M 1/1605* (2014.02); *A61M 1/267* (2014.02); *B01D 15/166* (2013.01); *B01D 15/18* (2013.01); *B01D 15/362* (2013.01); *B01D 15/363* (2013.01); *B01J 20/20* (2013.01); *B01J 20/2805* (2013.01); *B01J 39/02* (2013.01); *B01J 39/10* (2013.01); *B01J 39/12* (2013.01); *B01J 41/02* (2013.01); *B01J 41/10* (2013.01); *B01J 47/018* (2017.01); *B01J 47/024* (2013.01); *B01J 47/026* (2013.01); *B01J 47/12* (2013.01); *A61M 2205/3331* (2013.01)

(58) Field of Classification Search
CPC .............. A61M 1/1619; A61M 1/1635; A61M 1/1696; A61M 1/267; A61M 1/287; A61M 2205/3331; B01D 15/166; B01D 15/18; B01D 15/362; B01D 15/363; B01J 20/20; B01J 20/2805; B01J 2220/62; B01J 39/02; B01J 39/10; B01J 39/12; B01J 41/02; B01J 41/10; B01J 47/018; B01J 47/024; B01J 47/026; B01J 47/12
See application file for complete search history.

(56) References Cited

U.S. PATENT DOCUMENTS

| | | |
|---|---|---|
| 2013/0199998 A1 | 8/2013 | Kelly et al. |
| 2013/0213890 A1 | 8/2013 | Kelly et al. |
| 2014/0158588 A1 | 6/2014 | Pudil et al. |
| 2020/0078507 A1 | 3/2020 | Bluchel et al. |

OTHER PUBLICATIONS

Agar, John WM, Review: *Understanding sorbet dialysis systems*, Nephrology 15 (2010) pp. 406-411.
Ash, Stephen R., *Sorbent Dialysis Systems: An Expert Commentary by Stephen R. Ash, MD, FACP*, Medscape Nephrology, Aug. 5, 2008 (10 pages).
Charnow, J.A., (Jan. 3, 2014) *Dialysis patient death rate continues to drop*, Renal & Urology News, <https://www.renalandurologynews.com/home/news/hemodialysis/dialysis-patient-death-rate-continues-to-drop/>.
Couser et al., *The contribution of chronic kidney disease to the global burden of major noncommunicable diseases*, International Society of Nephrology, published online Oct. 12, 2011 (13 pages).
Gordon et al., *Zirconium Phosphate—A Potentially Useful Adsorbent In The Treatment Of chronic Uraemia\**, Proc. Eur. Dial. Trans. Assoc., 1968, 5:86-94.
Gordon et al., *A Sorbent Based Low Volume Recirculating Dialysate System*, Trans Amer Soc Artif Int Organs, vol. 15, 1969, p. 347.
McGill et al., *Sorbent Hemodialysis: Clinical Experience With New Sorbent Cartridges and Hemodialyzers*, ASAIO Journal 2008 (4 pages).
Neumann, M.E. (Jul. 2014), $20^{th}$ annual ranking: *A look back, and getting positioned for the future*, Nephrology News & Issues 26(8), pp. 30-31.
United States Renal Data System (URDS), *Chapter 9: Healthcare Expenditures for Persons with ESRD*, vol. 2, 2018 USRDS Annual Data Report (10 pages).
U.S. Renal Data System (URDS), 2018 Annual Data Report: Atlas Of End-Stage Renal Disease in the United States, National Institutes of Health, National Institute of Diabetes and Digestive and Kidney Diseases, Bethesda, MD, <https://www.usrds.org/previous-adrs/2010-2019/>.
International Search Report and Written Opinion for PCT/SG2021/050208 (ISA/EP) mailed Jul. 12, 2021 (9 pages).
International Preliminary Report on Patentability for PCT/SG2021/050208 (IPEA/EP) mailed Mar. 14, 2022 (7 pages).

Type II, Normal Concentrations, 300mL

| Set 1 | Ca | Mg | K | Phos |
|---|---|---|---|---|
| D0 | 1.2802 | 0.2029 | 2.014 | 1.129 |
| D1-D4 | 1.0340 | 0.1388 | 0.935 | 0.505 |
| D5-D8 | 1.1310 | 0.1560 | 0.937 | 0.666 |
| D9-D12 | 1.1270 | 0.1585 | 0.976 | 0.709 |
| D13-D16 | 1.1500 | 0.1604 | 0.976 | 0.729 |
| D17-D20 | 1.1420 | 0.1573 | 0.985 | 0.750 |
| Recovery | 87% | 76% | - | - |
| Removal | - | - | 52% | 41% |

Type II, High Phosphate Concentration, 300mL

| Set 5 | Ca | Mg | K | Phos |
|---|---|---|---|---|
| D0 | 1.2504 | 0.3150 | 2.0425 | 2.368 |
| D1-D4 | 0.9932 | 0.2040 | 1.053 | 1.235 |
| D5-D8 | 1.1140 | 0.2520 | 1.1887 | 1.500 |
| D9-D12 | 1.1208 | 0.2570 | 1.043 | 1.525 |
| D13-D16 | 1.2004 | 0.2930 | 0.971 | 1.547 |
| D17-D20 | 1.1464 | 0.2690 | 1.04975 | 1.567 |
| Recovery | 89% | 81% | - | - |
| Removal | - | - | 48% | 38% |

FIG. 17

Type II, High Potassium Concentration, 300mL

| Set 2 | Ca | Mg | K | Phos |
|---|---|---|---|---|
| D0 | 1.3420 | 0.3870 | 3.870 | 1.098 |
| D1-D4 | 1.1600 | 0.2900 | 1.386 | 0.516 |
| D5-D8 | 1.1088 | 0.2710 | 1.264 | 0.508 |
| D9-D12 | 1.2148 | 0.3250 | 1.621 | 0.593 |
| D13-D16 | 1.1392 | 0.2750 | 1.406 | 0.548 |
| D17-D20 | 1.0060 | 0.2070 | 1.469 | 0.586 |
| Recovery | 84% | 71% | - | - |
| Removal | - | - | 63% | 50% |

Type II, Low Calcium Concentration, 300mL

| Set 6 | Ca | Mg | K | Phos |
|---|---|---|---|---|
| D0 | 0.6512 | 0.2800 | 1.9593 | 0.908 |
| D1-D4 | 0.7280 | 0.2570 | 1.063 | 0.704 |
| D5-D8 | 0.6650 | 0.2410 | 1.074 | 0.648 |
| D9-D12 | 0.7472 | 0.3270 | 0.962 | 0.652 |
| D13-D16 | 0.7216 | 0.2870 | 0.6268 | 0.485 |
| D17-D20 | 0.6844 | 0.2730 | 0.9528 | 0.631 |
| Recovery | 109% | 99% | - | - |
| Removal | - | - | 52% | 31% |

FIG. 17 (cont.)

Type II, Very High Potassium Concentration, 300mL

| Set 3 | Ca | Mg | K | Phos |
|---|---|---|---|---|
| D0 | 1.2848 | 0.3280 | 5.748 | 1.176 |
| D1-D4 | 1.2732 | 0.3220 | 2.383 | 0.790 |
| D5-D8 | 1.2372 | 0.2950 | 2.469 | 0.853 |
| D9-D12 | 1.2604 | 0.3200 | 2.590 | 0.889 |
| D13-D16 | 1.2776 | 0.3330 | 2.298 | 0.869 |
| D17-D20 | 1.2272 | 0.2930 | 2.279 | 0.851 |
| Recovery | 98% | 95% | - | - |
| Removal | - | - | 58% | 28% |

Type II, Very High Potassium Concentration, 300mL

| Set 7 | Ca | Mg | K | Phos |
|---|---|---|---|---|
| D0 | 1.7800 | 0.2690 | 2.035 | 1.113 |
| D1-D4 | 1.0024 | 0.0890 | 0.899 | 0.541 |
| D5-D8 | 1.5852 | 0.2280 | 1.1015 | 0.763 |
| D9-D12 | 1.5596 | 0.2120 | 0.9538 | 0.750 |
| D13-D16 | 1.6500 | 0.2220 | 1.143 | 0.815 |
| D17-D20 | 1.5916 | 0.2060 | 0.9175 | 0.765 |
| Recovery | 83% | 71% | - | - |
| Removal | - | - | 51% | 35% |

FIG. 18

Type II, Low Phosphate Concentration, 300mL

| Set 4 | Ca | Mg | K | Phos |
|---|---|---|---|---|
| D0 | 1.2580 | 0.3090 | 1.9656 | 0.494 |
| D1-D4 | 1.0732 | 0.2650 | 0.8663 | 0.278 |
| D5-D8 | 1.1340 | 0.2540 | 1.042 | 0.333 |
| D9-D12 | 1.2280 | 0.2870 | 0.9895 | 0.355 |
| D13-D16 | 1.1900 | 0.2540 | 0.7835 | 0.344 |
| D17-D20 | 0.9900 | 0.1870 | 0.8538 | 0.324 |
| Recovery | 89% | 81% | - | - |
| Removal | - | - | 54% | 34% |

Type II, High Magnesium Concentration, 300mL

| Set 8 | Ca | Mg | K | Phos |
|---|---|---|---|---|
| D0 | 1.3064 | 0.8600 | 2.090 | 1.144 |
| D1-D4 | 1.3644 | 0.6830 | 1.182 | 0.835 |
| D5-D8 | 1.2060 | 0.7190 | 1.189 | 0.843 |
| D9-D12 | 1.2312 | 0.7220 | 0.932 | 0.774 |
| D13-D16 | 1.2068 | 0.6540 | 0.832 | 0.732 |
| D17-D20 | 1.1720 | 0.6090 | 0.643 | 0.659 |
| Recovery | 95% | 79% | - | - |
| Removal | - | - | 54% | 33% |

FIG. 18 (cont.)

DIALYSATE REGENERATOR COMPRISING REVERSIBLE RETAINER

CROSS-REFERENCE TO RELATED APPLICATION

This application is a National Stage Application, filed under 35 U.S.C. § 371, of International Application No. PCT/SG2021/050208, filed Apr. 13, 2021, which claims priority to SG Application No. 10202003361W, filed Apr. 13, 2020, and SG Application No. 10202003363P, filed Apr. 13, 2020, and SG Application No. 10202003365X, filed Apr. 13, 2020, the contents of all of which are hereby incorporated by reference in their entirety.

TECHNICAL FIELD

An aspect of the disclosure relates to a dialysate regenerator. Another aspect of the disclosure relates to a dialysis device including a dialysate regenerator. Another aspect of the disclosure relates to a medical use of the dialysate regenerator.

BACKGROUND

Sorbent-based regenerative dialysis systems provide renal replacement therapy just like conventional dialysis systems, while using an alternative method for dialysate generation. Traditional, single-pass dialysis systems send spent dialysate to the drain, while sorbent-based regenerative dialysis systems allow for the regeneration and reuse of dialysate through the use of sorbent materials.

This allows sorbent-based regenerative dialysis systems to use a much smaller volume of water than single-pass systems. This may eliminate the need for special infrastructure for water supply and drainage, and reduce consumption of electrical power, allowing sorbent-based regenerative dialysis systems to be used in a wider range of environments, including home environments. Similarly, sorbent technology allows for the creation of smaller dialysis systems with increased portability and ease of use.

All existing sorbent-based dialysate regeneration systems rely on either directly or indirectly contacting spent dialysate with a series of adsorber materials (see FIG. 1). Those can be classified in the following groups:
Activated Carbon: This sorbent removes organic uremic metabolites from spent dialysate, e.g., creatinine, uric acid and some middle molecules such as $\beta 2$ microglobulin.
Anion Exchanger: Most sorbent systems contain hydrous zirconium oxide (HZO) as an inorganic anion exchanger adsorbing negatively charged anions such as phosphate and sulfide in exchange for hydroxide. HZO also has some weak cation exchange properties, adsorbing bivalent and multivalent cations.
Urea adsorber: Due to the low reactivity and specificity of urea, the existing sorbent systems have to resort to a combination of enzyme catalyzed hydrolysis of urea, and subsequent adsorption of the hydrolysis product, ammonia, on a non-selective cation exchanger. This cation exchanger is usually zirconium phosphate (ZP), exchanging ammonium ions for sodium or hydrogen ions.
Zirconium Phosphate, however, also adsorbs other cations, most notably calcium, magnesium and potassium in exchange for sodium or hydrogen. This inadvertent electrolyte removal consumes cation exchange capacity (and thereby urea adsorption capacity) and impacts dialysate sodium concentration and acidity. Most crucially though, it necessitates an additional element for the dialysate reconstitution process, which is electrolyte re-infusion. Electrolyte re-infusion requires a controlled pumping system adding electrolytes to the regenerated dialysate in order to re-establish the physiologically required electrolyte concentrations. To this end, a solution of calcium, magnesium and/or potassium ions must be infused into the regenerated dialysate. The dispensed solution has to be prepared by the patient before treatment, or is provided in sterilised pre-packed form.

FIG. 2 shows a cross-sectional view of a conventional device currently using sorbent regenerative technology for peritoneal dialysis, and FIG. 3 illustrates schematically the basic elements of the sorbent regeneration process. Common to other types of dialysis systems, fresh dialysate is provided for the treatment of a patient. There, it takes up uremic solutes, electrolytes and fluid volume from the patient. Spent dialysate, containing uremic solutes and excess electrolytes that have been removed from the patient, is then purified as it passes through the sorbent. Uremic solutes are removed and electrolytes are set to their target concentrations. This usually requires an electrolyte infusion system (enrichment solution), adding necessary electrolytes to produce a regenerated dialysate that is then returned to the patient to continue the dialysis treatment.

By far the most extensively used sorbent-based regenerative hemodialysis device was the REDY system, introduced in 1973. The first generation of the machine weighed 60 pounds, making it the first portable machine for home hemodialysis.

The REDY sorbent cartridges provided dialysate regeneration by reprocessing used dialysate into fresh dialysate by passing it through a column of regenerative materials. The cartridge effluent was then mixed with a proportioned volume of infusate containing calcium, potassium, and magnesium to produce fresh dialysate as prescribed by the physicians.

Most of the alternative methods for sorbent-based dialysate regeneration focus on the central problem of urea removal. The key difficulty here is that urea is notoriously inert and unreactive, making its selective removal difficult. Several techniques thus still rely on the chemical modification of urea, followed by the selective adsorption or removal of the degradation products. For example, the use of a "Nano sorbent" was proposed, which still uses urease to selectively hydrolyse urea, followed by an ion exchange process on a clay-type ion exchanger. However, selectivity is limited and an electrolyte re-infusion system may still be required.

In another approach, an electrochemical method is used to break down urea into gaseous decomposition products. This "electro-oxidation" however is not very specific, and parallel degradation processes form unwanted by-products which are difficult to remove and constitute significant concerns for biocompatibility or even toxicity. Further, electrode lifespan and cost have to be considered.

There are also approaches using activated carbon for direct urea adsorption. To date, this still requires large sorbent cartridges and cumbersome regeneration processes.

In yet another approach, a method is proposed using direct urea adsorption on a polyaldehyde sorbent. This too is still in early phase of development and its viability for dialysate regeneration has yet to be established.

The only viable method for sorbent-based dialysate regeneration currently on the market invariably leads to irreversible adsorption of essential electrolytes. Accordingly, all current devices still have to rely on electrolyte re-infusion systems for functionality.

Therefore, there remains a need to provide improved dialysate regenerators with an improved or ameliorated control over the ions.

SUMMARY

In a first aspect, there is provided a dialysate regenerator. The dialysate regenerator may include a purification means. The dialysate regenerator may include at least one reversible retainer. The reversible retainer may include an ion reservoir. The dialysate regenerator may include a dialysate flow path. The dialysate flow path may include a dialysate inlet for receiving a dialysate. The dialysate flow path may include a dialysate outlet for dispensing the dialysate. The dialysate regenerator may include a pump connected to the dialysate flow path. The pump may be configured to generate a flow of the dialysate from the dialysate inlet via the reversible retainer and the purification means to the dialysate outlet. A direction of the dialysate flow path through the reversible retainer may be reversible.

According to various embodiments, the ion reservoir may include an ion exchanger.

According to various embodiments, the dialysate regenerator may include a volume control means configured to direct a predetermined volume of the dialysate from the dialysate inlet via the reversible retainer and the purification means to the dialysate outlet.

According to various embodiments, the ion reservoir may be in the form of particles, granules, beads, fabric, membrane, or a combination thereof.

According to various embodiments, the ion reservoir may be a reversible ion exchanger capable of retaining and releasing ions.

According to various embodiments, the ion reservoir may be an amphoteric ion exchanger.

According to various embodiments, the ion exchanger may change from being predominantly an anion exchanger at a pH value of below 5 to predominantly a cation exchanger at a pH value of above 8.

According to various embodiments, the ion reservoir may be hydrous zirconium oxide (HZO).

According to various embodiments, the ion reservoir may be present in a quantity of less than about 50 gram (g), or less than about 20 g for each of the at least one reversible retainer.

According to various embodiments, the ion reservoir may have an average particle size in the range of about 25 micrometer to about 100 micrometer, or about 50 micrometer to about 100 micrometer.

According to various embodiments, the ion reservoir in a pristine state may include ion salts.

According to various embodiments, the ion reservoir may be embedded in a filter pad and/or an additional sorbent bed.

According to various embodiments, the at least one reversible retainer may be positioned upstream of the purification means in a first direction of the dialysate flow path and positioned downstream of the purification means in a second direction of the dialysate flow path, wherein the second direction of the dialysate flow path is reverse to the first direction.

According to various embodiments, the reversible retainer may be configured to decrease the pH of a dialysate upstream of the purification means by retaining ions from the dialysate.

According to various embodiments, the reversible retainer may be configured to increase the pH of a dialysate downstream of the purification means by releasing ions into the dialysate.

According to various embodiments, the dialysate regenerator may include one reversible retainer positioned upstream of the purification means in a first direction of the dialysate flow path through the reversible retainer and the same positioned downstream of the purification means in a second direction of the dialysate flow path through the reversible retainer, wherein the second direction of the dialysate flow path is reverse to the first direction of the dialysate flow path through the reversible retainer.

According to various embodiments, the dialysate regenerator may include one or more valves for alternating the dialysate flow path between a first flow phase from the dialysate inlet to the temporary storage volume via the reversible retainer; and a second flow phase from the temporary storage volume to the dialysate outlet via the purification means and the reversible retainer, wherein a direction of the dialysate flow path through the reversible retainer in the second flow phase is reverse to the direction of the dialysate flow path through the reversible retainers in the first flow phase.

According to various embodiments, the dialysate regenerator may include a first reversible retainer upstream of the purification means and a second reversible retainer downstream of the purification means.

According to various embodiments, the dialysate regenerator may include one or more valves for alternating the direction of the dialysate flow path through the reversible retainer between a first direction and a second direction, the second direction being reverse to the first direction of the dialysate flow path through the reversible retainer.

According to various embodiments, the dialysate regenerator may include a volume control means configured to direct a predetermined volume of the dialysate from the dialysate inlet via the reversible retainer and the purification means to the dialysate outlet, wherein the volume control means comprises a fluid portioning system to divide a dialysate flow into uniform portions for sequential regeneration.

According to various embodiments, the dialysate regenerator may include one or more valves for alternating the dialysate flow path between the dialysate inlet and the dialysate outlet in a first state via the reversible retainer, the purification means, the reversible retainer and in a second state via the reversible retainer, the purification means, the reversible retainer, wherein a direction of the dialysate flow path through the reversible retainers in the second state is reverse to the direction of the dialysate flow path through the reversible retainers in the first state.

According to various embodiments, the dialysate regenerator may include a fluid portioning system to divide a dialysate flow into uniform portions for sequential regeneration.

According to various embodiments, the dialysate regenerator may include one or more valves for alternating the direction of the dialysate flow path through the reversible retainer between a first direction and a second direction, the second direction being reverse to the first direction.

According to various embodiments, the dialysate regenerator may include a pressure sensor.

According to various embodiments, the one or more valves may be synchronized and alternate the direction of the dialysate flow path through the reversible retainer upon a pressure change detected by the pressure sensor.

According to various embodiments, the dialysate regenerator may include a temporary storage volume.

According to various embodiments, the dialysate regenerator may include a flow adjuster, optionally comprising a pressure sensor.

In a second aspect, there is provided use of an ion reservoir in the manufacture of a dialysate regenerator including said ion reservoir included in at least one reversible retainer for the treatment of a patient suffering from renal insufficiency, liver failure or respiratory insufficiencies with abnormally high levels of one or more toxins or insufficient removal of metabolic waste products or $CO_2$, said treatment including moving a dialysate of the patient through a dialysate flow path including a dialysate inlet for receiving a dialysate by action of a pump, a dialysate outlet for dispensing the dialysate, and a purification means, wherein a flow of the dialysate is generated from the dialysate inlet via the reversible retainer and the purification means to the dialysate outlet, wherein a direction of the dialysate flow path through the reversible retainer is reversible.

In a third aspect, there is provided a dialysis device including the dialysate regenerator as described above.

In a fourth aspect, there is provided a dialysate regenerator as described above for use in therapy.

In a fifth aspect, there is provided a method of treating a patient suffering from renal insufficiency, liver failure or respiratory insufficiencies with abnormally high levels of one or more toxins or insufficient removal of metabolic waste products or $CO_2$, the method including moving a dialysate of the patient through a dialysate flow path including a dialysate inlet for receiving a dialysate by action of a pump, a dialysate outlet for dispensing the dialysate, and a purification means, wherein a flow of the dialysate is generated from the dialysate inlet via a reversible retainer including an ion reservoir and the purification means to the dialysate outlet, wherein a direction of the dialysate flow path through the reversible retainer is reversible.

BRIEF DESCRIPTION OF THE DRAWINGS

The invention will be better understood with reference to the detailed description when considered in conjunction with the non-limiting examples and the accompanying drawings, in which:

FIG. 17 shows Tables of the results with the optimised reversible retainer performance;

FIG. 18 shows Tables of the results with the optimised reversible retainer performance;

DETAILED DESCRIPTION

Figure 1:
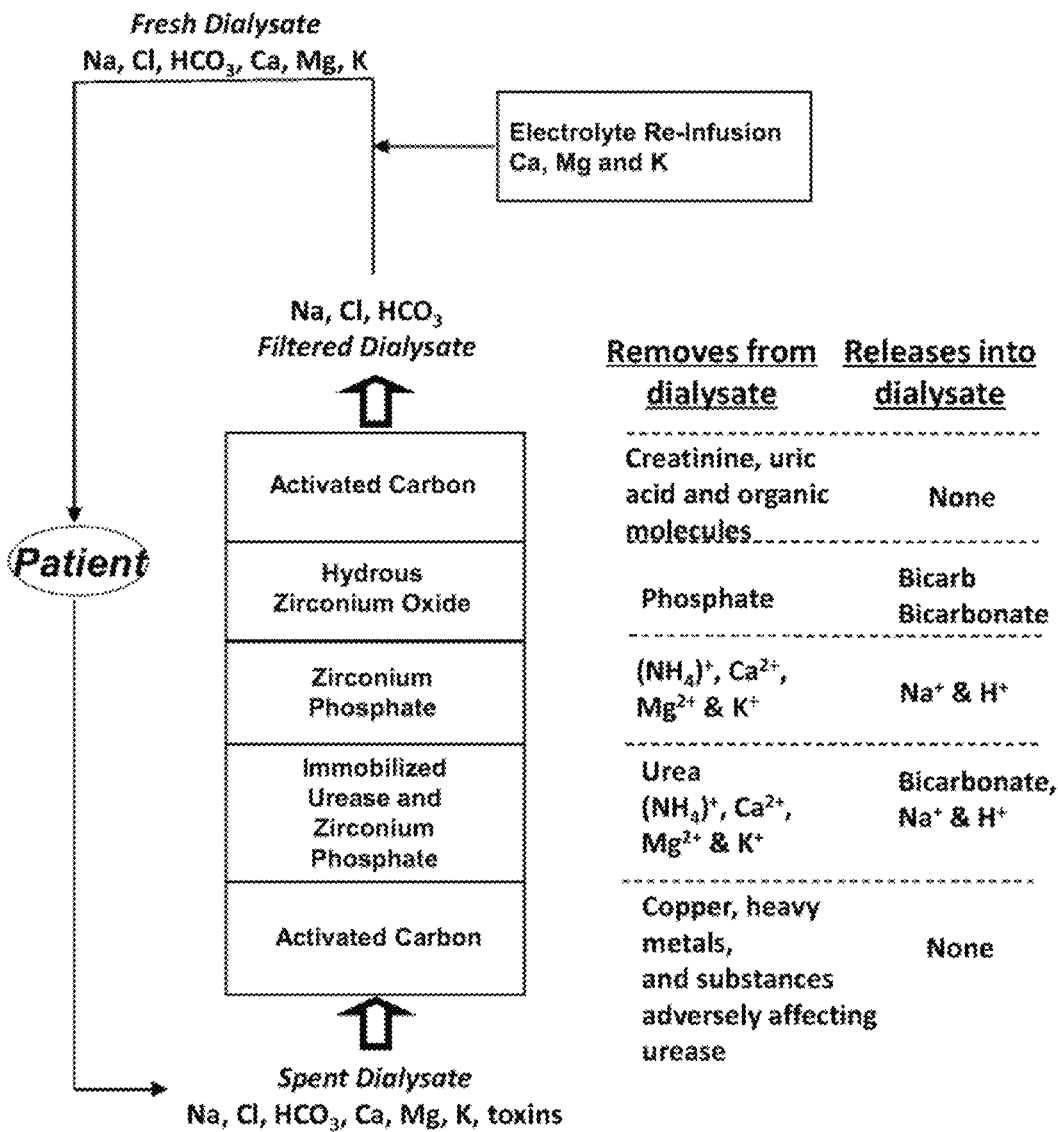
FIG. 1 shows a schematic for a typical sorbent cartridge used for regeneration of hemodialysate.

The following detailed description refers to the accompanying drawings that show, by way of illustration, specific details and embodiments in which the disclosure may be practiced. These embodiments are described in sufficient detail to enable those skilled in the art to practice the disclosure. Other embodiments may be utilized and structural, and logical changes may be made without departing from the scope of the disclosure. The various embodiments are not necessarily mutually exclusive, as some embodiments can be combined with one or more other embodiments to form new embodiments.

In a first aspect, the present disclosure refers to a dialysate regenerator 100. The dialysate regenerator 100 may include a purification means 110. The dialysate regenerator 100 may include at least one reversible retainer 120. The at least one reversible retainer 120 may include an ion reservoir. The dialysate regenerator 100 may include a dialysate flow path. The dialysate flow path may include a dialysate inlet 130 for receiving a dialysate. The dialysate flow path may include a dialysate outlet 140 for dispensing the dialysate. The dialysate regenerator 100 may include a pump 150 connected to the dialysate flow path. The pump 150 may be configured to generate a flow of the dialysate from the dialysate inlet 130 via the reversible retainer 120 and the purification means 110 to the dialysate outlet 140. A direction of the dialysate flow path through the reversible retainer 120 may be reversible.

As used herein, and in accordance with various embodiments, the term 'dialysis' may refer to hemodialysis, hemofiltration, hemodiafiltration, plasmapheresis, peritoneal dialysis, liver dialysis, lung dialysis, water purification, regeneration of physiological fluids, or regeneration of biological fluids. Similarly a dialysate regenerator 100 may refer to a dialysate regenerator 100 for hemodialysis dialysate, a dialysate regenerator 100 for peritoneal dialysis dialysate, a dialysate regenerator 100 for liver dialysis dialysate, a dialysate regenerator 100 for lung dialysis dialysate, a regenerator for regeneration or purification of water, a dialysate regenerator for regeneration of hemofiltrate, a dialysate regenerator for regeneration of plasma, a dialysate regenerator for regeneration of physiological fluids, or a dialysate regenerator for regeneration of biological fluids.

The dialysate regenerator 100 according to the present disclosure may include a purification means 110, also referred to as a purification compartment. The purification means may include toxin removal means. As used herein, and in accordance with various embodiments, the term 'purification means' may refer to a compartment that can contain one or more sorbent materials. The purification means may also include electro-oxidation means, electrodialysis means or other purification means that are not based on sorbent technology. The compartment can be connected to a dialysate flow path. The sorbent materials in the purification means 110 are used for removing specific solutes from solution, such as urea. The purification means 110 can have a single compartmental design wherein all sorbent materials necessary for performing dialysis are contained within the single compartment. Alternatively, the purification means 110 can have a modular design wherein the sorbent materials are dispersed across at least two different modules, which can be connected to form a unitary body. The purification means 110 in the present disclosure may be a disposable purification means 110.

The dialysate regenerator 100 according to the present disclosure may include at least one reversible retainer 120 including or comprising an ion reservoir. As used herein, and in accordance with various embodiments, the term 'reversible retainer' may refer to a component that retains ions in one flow direction of a dialysate and releases said ions in a reverse flow direction of a dialysate. The reversible retainer 120 may therefore comprise an ion reservoir. The ion reservoir may be any chemical compound capable of retaining and releasing ions. Examples of such compounds may be an ion exchanger, an ion exchange membrane, an ion rejection membrane, etc. The retaining and releasing of the ions may be influenced by parameters of the dialysate, for example, by the pH value, the temperature, the pressure, the concentration, the toxin or electrolyte concentration, the density and the viscosity. According to one embodiment, the ion reservoir retains and releases ions dependent of the pH value. As used herein, and in accordance with various embodiments, the term 'ion' when used in connection with the ion reservoir may refer to a charged atom or molecule. In particular, the ion may be a cation. The ion may be a cationic atom. The ion may be a physiologically essential ion. The ion may comprise a cation of the second group of the periodic table. Advantageously, since the essential ion is selected from the second group of the periodic table, it has a higher valence than, for example, a cation from the first group of the periodic table. The higher valence, in turn, affects that the cation having a higher valence may have a greater affinity for the ion reservoir or the ion exchanger contained in the reversible retainer. The ion may comprise calcium. The ion may comprise magnesium. The ion may comprise potassium. The ions, such as calcium, magnesium and potassium, may be termed essential ions, due to their physiological relevance.

The dialysate regenerator 100 according to the present disclosure may include a pump 150. As used herein, and in accordance with various embodiments, the term 'pump' is meant to refer to any pumping means. Particularly, it may include a volume control means 115 configured to direct a predetermined volume of the dialysate from the dialysate inlet 130 via the reversible retainer and the purification means 110 to the dialysate outlet 140. Additionally or alternatively, it includes both an actuator which uses suction or pressure to move a dialysate, and a motor for mechanically moving the actuator. Suitable pump actuators may include an impeller, piston, diaphragm, the lobes of a lobe pump, screws of a screw pump, rollers or linear moving fingers of a peristaltic pump, or any other mechanical construction for moving dialysate. It may also include a bellow pump, gear pump, and rotary vane pump. The pump is connected to the dialysate flow path for pumping dialysate through the dialysate flow path from a dialysate inlet 130 for receiving a dialysate to a dialysate outlet 140 for dispensing the dialysate. The pump 150 may be in a feedback loop or closed loop control and may respond to pressure changes caused by variations in the dialysate flow detected at the dialysate inlet or outlet, for example at a pressure sensor. In a continuous dialysis, the pump 150 may actively regulate the flow rate of dialysate regeneration in response to fluid supply or demand detected at the dialysate inlet or outlet. The pump 150 may also be configured to operate independently and to produce a desired dialysate flow across the dialysate regenerator, for example to provide a desired dialysate flow for a dialysis treatment.

The pump may include at least one volume control means 115, also referred to as a fluid control compartment. With reference to various embodiments described further below and in the case of a single reversible retainer, the volume control means 115 may have the form of a temporary storage volume 180. In the case of more than a single reversible retainer, the volume control means 115 may have the form of a fluid portioning system 160. In these embodiments, the volume control means 115 may ensure that the same concentration of essential ions is returned to the same volume of dialysate, so as to keep the concentration of essential ions constant per aliquot of dialysate.

The dialysate entering the dialysate flow path at the dialysate inlet 130 may be termed 'spent dialysate' and may refer to a dialysate that contains one or more toxins, or waste species, or waste substance, such as urea. It is generally understood that it is intended to remove such one or more toxins, or waste species, or waste substance, such as urea from the spent dialysate. The spent dialysate may also contain one or more electrolytes or ions. In accordance with the disclosure, it may be desired to retain these electrolytes or ions in the dialysate. The term "retain" in context with the essential ions may refer to a substantial amount of the essential ions being retained as compared to the spent dialysate. For example, more than 80% of calcium and magnesium ions may be retained, or about 50% of potassium ions. The retention rate is dependent on the ion and/or the concentration thereof. It is desired that a fixed molecular amount of essential ions may be retained per volume of dialysate, and that any excess is allowed to pass through, which may be adsorbed in the purification means. It is also advantageous to retain about 50% of potassium ions on the reversible retainer, compared to more than 80% of calcium and magnesium ions, since this will allow to provide substantial net removal of potassium in the purification means (considered harmful if not removed) from the patient.

The dialysate dispensed at the dialysate outlet 140 may be termed 'fresh dialysate' and may refer to a dialysate that is substantially free of one or more toxins, or waste species, or waste substance, such as urea. The fresh dialysate may also contain a desired concentration of one or more electrolytes or ions.

The purification means 110 and the at least one reversible retainer 120 including an ion reservoir are connected via the dialysate flow path and are positioned between the dialysate inlet 130 and the dialysate outlet 140. The term 'via' does not imply a sequence of the purification means 110 and the at least one reversible retainer 120 within the dialysate flow path. However, it is understood that a dialysate may be passed through the at least one reversible retainer 120 before being passed through the purification means 110. Subsequently, after being passed through the purification means 110, the dialysate may be passed through the at least one reversible retainer 120 in a reverse direction, which may be the same reversible retainer 120 the dialysate passed through before the purification means 110, or it may be a different reversible retainer. Accordingly, the pump 150 generates a flow of the dialysate from the dialysate inlet 130 via the reversible retainer 120 and the purification means 110 to the dialysate outlet 140. The flow is configured to pass through the reversible retainer 120, then through the purification means 110, then through the same or another reversible retainer in a reverse direction. Hence, the dialysate may be configured to be passed through the at least one reversible retainer 120 at least twice, but in opposite directions, and between these at least two times the dialysate may be passed through the purification means 110. Accordingly, a direction of the dialysate flow through the reversible retainer may be reversible. The flow directions may be controlled by volume control means 115. In particular, the volume control means 115 may ensure that the volumes of dialysate are equal in both flow directions.

The dialysate flow may be an intermittent flow, optionally a tidal flow. Advantageously, when using a tidal flow, the dialysate inlet 130 for receiving the dialysate and the dialysate outlet 140 for dispensing dialysate may be combined into a single access site. Having only a single access site for both dialysate inlet 130 and dialysate outlet 140 permits for relying only on a single percutaneous access location, which minimizes the risk of infection in both the home and out-of-the-home environments. In the tidal flow, the pump 150 may provide for flow modes within the dialysate flow path. One flow mode may refer to each volume of dialysate that is passed through the dialysate flow path at one time. In each flow mode, about 100 milliliter (mL) to about 500 mL, or about 150 mL to about 400 mL, or about 200 mL to about 300 mL, optionally about 250 mL of dialysate may be moved through the dialysate flow path. In these ranges, the combined amount of essential bivalent ions (e.g. calcium and magnesium) in the spent dialysate that are to be retained by the reversible retainer 120 may be below about 1 millimol (mmol), or below 0.5 mmol, or below 0.4 mmol. Accordingly, the concentration of the essential bivalent ions that are retained is about 1 to 3 mmol/L, or about 2 mmol/L. Such low amounts of essential ions to be retained allows for a low amount of the ion reservoir (such as the ion exchanger), which, in turn, saves on space and weight of the dialysate regenerator 100.

Alternatively, the dialysate flow may be a continuous flow. In a continuous flow, the dialysate may typically have a flow rate through the dialysate flow path of about 100 mL/min to about 500 mL/min, or about 200 mL/min to about 400 mL/min, or about 250 mL/min to about 350 mL/min. Other flow rates above and below may be considered.

The disclosure proposes to break with the existing paradigm of inadvertent ion adsorption and the requirement for re-infusion in sorbent-based dialysate regeneration systems. This is achieved by temporary retaining essential ions (e.g., calcium and magnesium) onto at least one reversible retainer 120 containing an ion reservoir, which is simply backwashed with regenerated dialysate to retrieve the ions (see, FIG. 4). Advantageously, such a dialysate flow path may provide a dialysate regenerator 100 with an improved or ameliorated control over the ions. The improved or ameliorated control over the essential ions may be due to the at least one reversible retainer 120 including an ion reservoir, which retains ions in the first direction of the dialysate flow path, and releases the same ions in a reverse direction of the dialysate flow in the dialysate flow path through reversible retainer 120. This system allows for essential ions, such as calcium and magnesium, to be retained before the dialysate is passed through the purification means 110, and to be released into the dialysate after being passed through the purification means 110. Accordingly, the dialysate regenerator 100 does not require electrolyte re-infusion, which is advantageous since it simplifies the dialysate regenerator, makes it easier to use, and allows to save on space, cost and material. Further advantageously, the retention of essential ions such as calcium and magnesium avoids wasting purification means capacity for the undesired adsorption of essential ions, allowing to reduce the size and cost of the purification means. In a typical sorbent system, this may save more than 25% of the sorbent capacity, e.g. it may save 30% to 50% of the cartridge capacity, which may translate into a possible size reduction of the device by 30% to 50%. Further advantageously, the retention of essential ions such as calcium and magnesium avoids excessive release of other ions, such as sodium, in exchange for calcium and magnesium, thus avoiding unwanted sodium fluctuations in regenerated dialysate, which are a key challenge for conventional sorbent systems.

The dialysate flow path may include one or more valves (see, FIG. 4) for alternating the direction of the dialysate flow path through the reversible retainer 120 between a first direction and a second direction, the second direction being reverse to the first direction.

The ion reservoir may comprise an ion exchange membrane, an ion exchanger, reversible precipitation means, an ion rejection membrane, or other reversible ion retention means. Advantageously, the dialysate flow flows directly through the ion reservoir, meaning that the ion reservoir is positioned between an inlet and an outlet of the reversible retainer. Therefore, the dialysate flow is in a convective mode, and the ion exchange membrane or ion rejection membrane would also be used in a convective mode, instead of in a diffusion mode. Advantageously, when an ion exchanger is used, the dialysate flow path does not have to undergo selective diffusion across a membrane. This allows full efficiency of purification at high exchange flow rates, low flow resistance and low cost. Furthermore, an ion exchanger may be advantageous over the use of an ion exchange membrane or ion rejection membrane, since the ion exchange membrane may have a high flow resistance and high material cost, thus presenting a serious drawback for their application together with a disposable cartridge. The convective mode is also particularly advantageous when using an ion exchanger in the form of particles.

As used herein, and in accordance with various embodiments, the term 'ion exchanger' may be molecules consisting of both a stable high molecular weight backbone structure and active ionic groups. The backbone provides stability, insolubility, and structure, while the active groups provide ion exchange properties. The backbone may include any element or combination of elements that can be joined together to form long, preferably branched chains or 3-dimensional networks. The ion exchanger may comprise an organic ion exchanger and an inorganic ion exchanger. The ion exchanger may be crystalline or amorphous. The property of insolubility imparted by this backbone structure may account for the nontoxicity of these agents. Since the ion exchanger is not soluble, it is not dissolved when used in dialysate regeneration.

The ion exchanger may comprise active groups, optionally selected from negatively charged anionic groups or positively charged cationic groups. The negatively charged groups may comprise sulfonate groups, carboxy groups, sulfate, sulfinate, phosphate, phosphonate, phosphinate, hydroxide, sulfide, (metal) oxyanions. The positively charged groups may comprise amino groups (primary, secondary, tertiary, qaternary, imino, zeolites (aluminosilicates), metal oxides, hydrous metal oxides, acidic salts of polyvalent metals, insoluble salts of heteropolyacids. The active groups determine the major properties of the ion exchangers. When negatively charged anionic groups, such as sulfonate or carboxy groups, are attached to the backbone structure, they impart a fixed negative charge, which is balanced by positively charged mobile cations. These cations can be exchanged and the compound therefore constitutes a cation exchanger.

Positive groups such as quaternary amines attached to the backbone impart a positive charge that is balanced by negatively charged mobile anions. These anions can be exchanged, and such compounds correspondingly represent anion exchangers. Amphoteric ion exchangers have both negative and positive active groups and can exchange both cations and anions. The ion exchanger may be present as porous structures. The porosity, the pore size, and the number and type of active group's represent the major determinants of the sorbents function. Ion exchangers may be viewed as electrolyte sponges. With greater selectivity coefficient for a certain cation, more of this cation will be bound as compared to a cation with lower selectivity. Most cation exchangers show the following selectivity for physiologically significant cations: $Li<Na<K \approx NH_4<<Mg<Ca$.

Thus, of this series, $Ca^{2+}$ has the greatest affinity for a typical cation exchanger. As a general rule, the higher the valence of a cation, the greater its affinity. For ions of the same valence, affinity is generally directly related to molecular weight. This specificity order means that a dialysate exchange process will result in calcium adsorption if calcium is present in the biologic fluid. This may result in unwanted consumption of adsorptive capacities and depletion of ions whose removal is not part of the intended therapeutic goal. Since biologic fluids are polyelectrolyte solutions, ion exchanger design for specific clinical purposes is limited by the nonspecificity of the exchange process and the relative affinities of the various ions for the exchangers.

The affinity may vary with different ion exchangers and may, within limits, be modified by the processes used to synthesise or pretreat ion exchangers prior to use.

The maximum capacity of an ion exchanger (i.e. its exchange potential or efficiency) is determined by the number of active groups, usually expressed in milliequivalents per gram of exchanger. This capacity can be determined by titrating the ion exchanger, just as is done in determining the concentration of an acid or base. However, the capacity for the desired ion under actual conditions of clinical use is of even greater practical interest. This is usually determined empirically under the actual conditions of use.

The capacity of the ion exchanger for the ion to be adsorbed may not only be dependent upon the theoretical capacity but also upon the selectivity coefficient and concentration of the ion to be removed. Competitive binding by other ions may also limit achieving full theoretical capacity. The action of certain ion exchangers may also be pH dependent, thereby limiting medical application to those, which are active either at or near the pH of body fluids. Such dependencies can be exploited to achieve reversible ion adsorption.

Further, the total exchange capacity for a cation with comparatively low selectivity coefficient is strongly dependent on the cation's concentration. In consequence, this cation may be adsorbed from more concentrated solutions, and desorbed into more diluted solutions.

The capacity of the ion exchanger according to this disclosure may be selected such that the essential ions are not quantitatively retained. Accordingly, the dialysate, after passing through the reversible retainer 120 for the first time, may still contain some of the essential ions, which are subsequently absorbed in the purification means 110. The capacity may for example be selected such that an undesired excess of essential ions is allowed to pass through the retainer, such that the excess will be adsorbed in the purification means 110. Advantageously, this can be used to correct patient imbalances, where the patient suffers from excess concentration of the essential ions.

The ion exchanger may be a cation exchanger or an anion exchanger. The ion reservoir may be in the form of particles, granules, beads, fabric, membrane, or a combination thereof. The ion reservoir may be a reversible ion reservoir capable of retaining and releasing ions. Optionally, the ion reservoir may comprise an amphoteric ion exchanger. The ion exchanger may change from being predominantly an anion exchanger at a pH value of below about 5, or below about 6, or below about 7. The ion exchanger may change from being predominantly a cation exchanger at a pH value of about above 8, or about above 7, or about above 6. Advantageously, since the ion exchanger may be an amphoteric ion exchanger and change its behavior according to pH value, the ion exchanger is capable of retaining ions at a certain pH value of the dialysate and releasing ions at a different pH value of the dialysate. Advantageously, the dialysate before passing through the at least one reversible retainer 120 and/or the purification means 110 may have a different pH value than the dialysate after passing through the purification means 110 and flowing towards the at least one reversible retainer 120 in the reverse direction. Additionally or alternatively, some essential ions may have a higher affinity for retention dependent on the pH of the dialysate. For example, the affinity of calcium (Ca) vs protons is dependent on pH value. At a high pH value (or a high calcium concentration), calcium is bound and protons are released. At low pH values (or low Ca concentration), protons are bound and Ca is released.

Accordingly, in some embodiments, the disclosure exploits two features that result in the synergistic effect of retaining and releasing ions from the dialysate, which obviates the need for an electrolyte re-infusion. On one hand, the amphoteric character of the ion exchanger causes the reversible retainer 120 to retain essential ions in one flow direction and to release these essential ions in the reverse direction. On the other hand, the pH value of the dialysate decreases after being passed through the reversible retainer 120 and the purification means 110. This is so since the dialysate returning from the purification means 110 has generally a slightly lower pH (approximately 6.5-7.2) than dialysate coming from the patient (approximately 7.4). The exchange of essential ions (such as Ca and Mg) for H and Na in the reversible retainer 120 already lowers the pH of the spent dialysate entering the purification means 110. The dialysate exiting the purification means 110 has a formally increased $pCO_2$, resulting in a further slight decrease of pH value of the dialysate. This lower pH facilitates the reversed exchange of H and Na against the previously retained essential ions (such as Ca and Mg) in the reversible retainer 120 when the dialysate is passed through the reversible retainer 120 in the reverse direction. Hence, the interplay between the ion reservoir being amphoteric and the purification means 110 decreasing the pH value of the dialysate may result in the synergistic effect as described above. It is understood, that this interplay is a non-limiting embodiment of the disclosure, and the omission of the electrolyte re-infusion may also be achieved by other means described herein.

The ion exchanger may be hydrous zirconium oxide (HZO). HZO may generally be considered an anion exchanger. It is used in dialysate regeneration and water purification to adsorb phosphate, fluoride and other potentially harmful anions. It was found that HZO also has amphoteric character, exchanging anions at pH<7, and cations at pH>7. The ion exchange properties can be represented by the following Scheme:

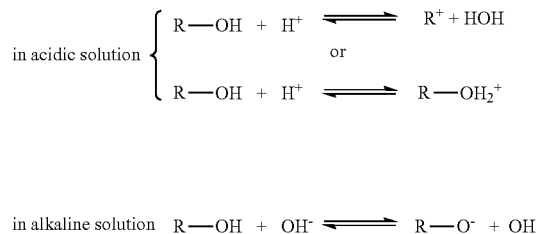

Scheme 1: pH-Dependent ion exhange properties of hydrous zirconium oxide

Advantageously, HZO appears to be unique in that it has a high degree of homogeneity of active groups within the matrix of HZO, which may advantageously allow for a finely tunable pH dependency of the reversability of the ion exchange process. This property was likely the key factor for the very good results obtained with this material.

The ion reservoir may be embedded in a filter pad. Additionally or alternatively, the ion reservoir may be embedded in an additional sorbent bed. The ideal arrangement for the reversible retainer 120 including the ion reservoir may be in a small sorbent bed, which is in sequential arrangement to the purification means 110 such that both, spent dialysate delivered to the main sorbent and fresh dialysate returning from the purification means 110 has to pass through this sorbent bed, using direct filtration in two distinct flow modes. In contrast to previously described diffusion controlled processes, direct filtration is highly efficient with low flow resistance and high fluid exchange and purification rates. It is suitable for cost efficient miniaturization and opens the way to the development of the first sorbent dialysis system, which does not depend on electrolyte re-infusion.

The ion reservoir may be comprised in the reversible retainer 120 in a quantity of less than about 50 gram, or less than 20 gram (g), or less than about 15 g, or less than about 10 g, or less than about 5 g, for each of the at least one reversible retainer 120. Advantageously, such low amounts of the ion reservoir may be advantageous in reducing the overall size of the dialysate regenerator 100.

The ion reservoir may have an average particle size in the range of about 25 micrometer to about 100 micrometer, or about 50 micrometer to about 100 micrometer. Such particle size ranges may be obtained by sieving the ion reservoir material prior to use. Advantageously, a particle size range of about 25 micrometer to about 100 micrometer, and more preferably of about 50 micrometer to about 100 micrometer gave the lowest pressure drop and fastest achievable dialysate flow rates.

The ion reservoir in a pristine state may refer to an ion reservoir prior to its first use. The ion reservoir in a pristine state may include essential ions. The essential ions may be included in the ion reservoir subsequent to a pretreatment with ion salts, and the ion reservoir may accordingly be preloaded with the essential ions. The ion salts may be the salts of the same ions that are to be retained and released in the ion reservoir. Advantageously, when the ion reservoir in a pristine state includes essential ions, one of the key challenges for optimization, namely the tendency of the ion reservoir to undergo gradual changes during use, can be avoided. Thus, without the ion reservoir in a pristine state including essential ions, usually, ion retention rates, such as Ca and Mg retention rates, were low at the beginning of the experiments and only reached satisfactory levels after lengthy periods of stabilization.

Accordingly, in one aspect, the ion exchanger may comprise a preselected percentage of essential ions, such as Ca and Mg. The preselected percentage may be a percentage of 0.1 to 10 wt % of Ca and/or Mg.

The at least one reversible retainer 120 may be positioned upstream of the purification means 110 in a first direction of the dialysate flow path through the reversible retainer and positioned downstream of the purification means 110 in a second direction of the dialysate flow path through the reversible retainer, wherein the second direction of the dialysate flow path is reverse to the first direction. The reversible retainer 120 may decrease the pH value of a dialysate upstream of the purification means 110 by retaining ions from the dialysate. The reversible retainer 120 may increase the pH value of a dialysate downstream of the purification means 110 by releasing ions into the dialysate.

Figure 4:
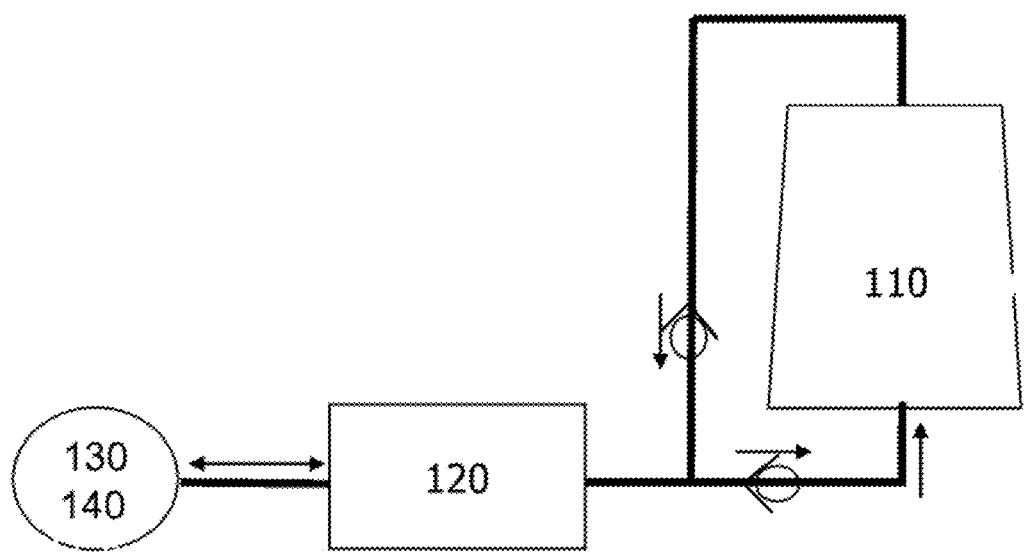
FIG. 4 is a schematic illustrating the basic elements of the disclosed dialysate regenerator.

In one embodiment, the dialysate regenerator 100 may include one reversible retainer 120. Said one reversible retainer 120 may be positioned upstream of the purification means 110 in a first direction of the dialysate flow path through the reversible retainer and the same reversible retainer may be positioned downstream of the purification means 110 in a second direction of the dialysate flow path through the reversible retainer, wherein the second direction of the dialysate flow path is reverse to the first direction. This embodiment is illustrated in FIG. 4.

Figure 5A:
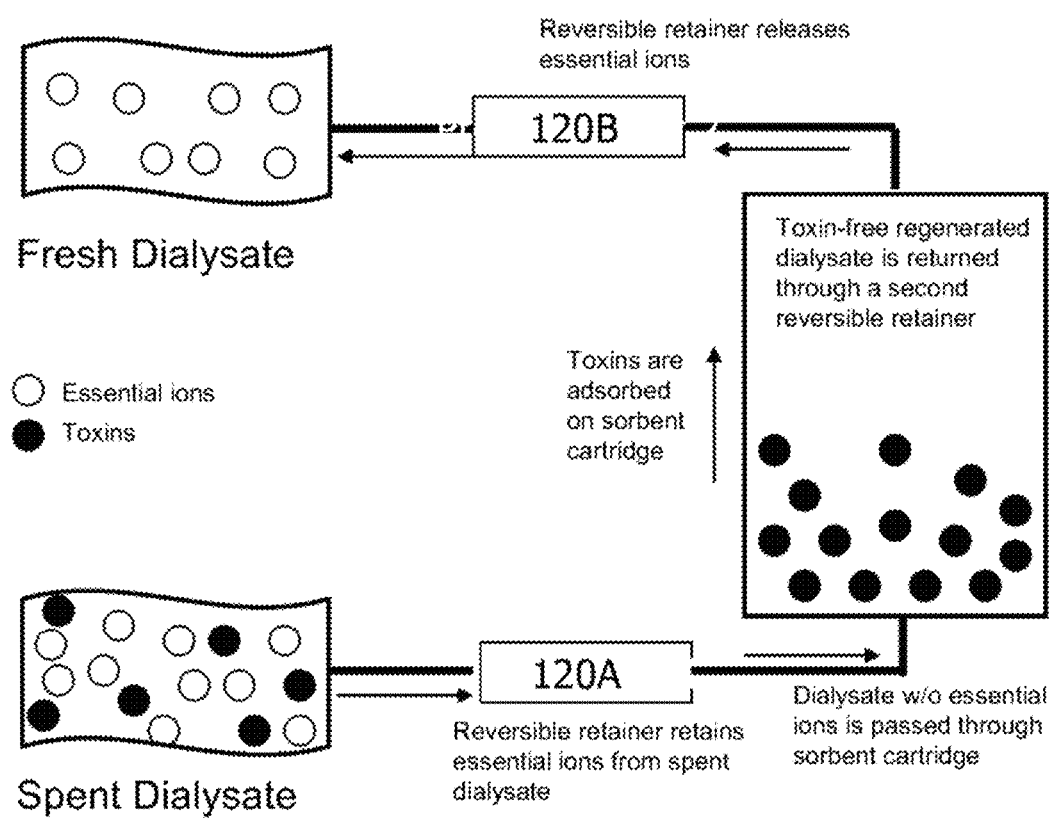
FIG. 5A is a schematic showing the dialysate regenerator in accordance with some embodiments of the disclosure in a first state ST1.
Figure 5B:
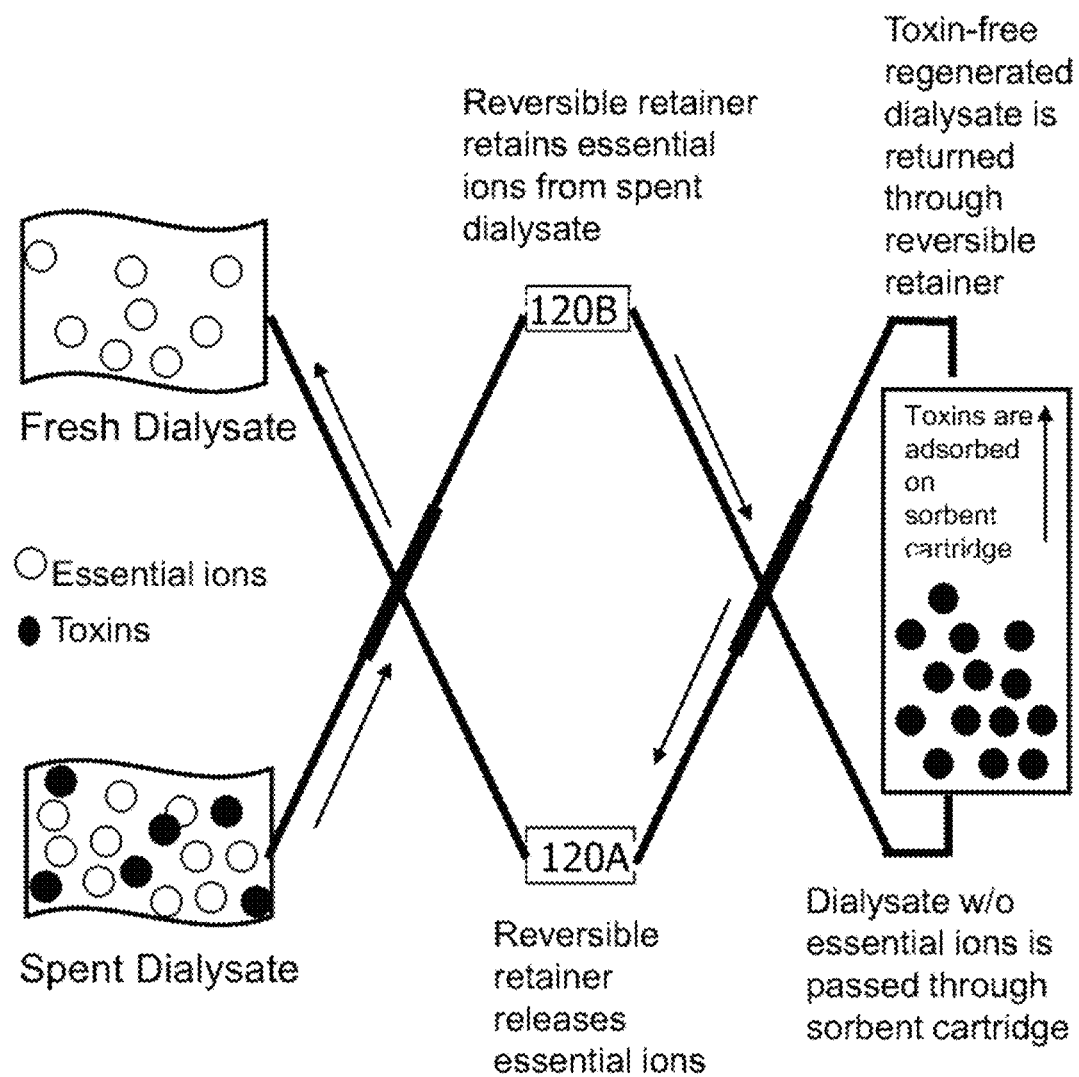
FIG. 5B is a schematic showing the dialysate regenerator in accordance with some embodiments of the disclosure in a first state ST2.

In another embodiment, the dialysate regenerator 100 may include a first reversible retainer 120A upstream of the purification means 110 and a second reversible retainer 120B downstream of the purification means 110. The dialysate regeneration may be carried out in sequential regeneration, and may include two alternate states including a first state and a second state. This embodiment is illustrated in FIG. 5A and FIG. 5B. Each of FIG. 5A and FIG. 5B, respectively, shows two alternate states. FIG. 5A shows a first state, ST1, wherein dialysate, containing essential ions and toxins, passes through a first reversible retainer 120A. The essential ions are retained at the ion reservoir comprised in reversible retainer 120A. The dialysate then passes through the purification means 110, wherein toxins are removed from the dialysate. The dialysate then passes through the reversible retainer 120B and essential ions previously retained by reversible retainer 120B are released into the dialysate. FIG. 5B shows a second state, ST2, with a reversed flow direction through the reversible retainers. In FIG. 5B, dialysate containing essential ions and toxins, passes through a first reversible retainer 120B. The essential ions are retained at the ion reservoir comprised in reversible retainer 120B. The dialysate then passes through the purification means 110, wherein toxins are removed from the dialysate. The dialysate then passes through the reversible retainer 120A and essential ions previously retained by reversible retainer 120A are released into the dialysate. By alternating the flow direction between ST1 and ST2, the reversible retainers 120A and 120B function as either retaining or releasing the essential ions, wherein each of the reversible retainers 120A and 120B retain the essential ions in a first direction upstream of the purification means 110, and release the essential ions in a second direction downstream of the purification means 110, i.e. in a reverse direction. This arrangement allows to effectively run the regeneration in a continuous flow of dialysate, which is divided (portioned) into the two alternating states. The setup is preferably combined with a fluid portioning system 160 which directs the switching between the two states such that the treated volumes of dialysate are identical for both states.

As described above in context with the pump and in accordance with this embodiment, the dialysate regenerator 100 may additionally include a fluid portioning system 160 (see, FIG. 6C) which may also function as a pump, to divide a dialysate flow into uniform portions for the sequential regeneration. The fluid portioning system 160 may include divide a dialysate flow into uniform portions for sequential regeneration.

Figure 6A:
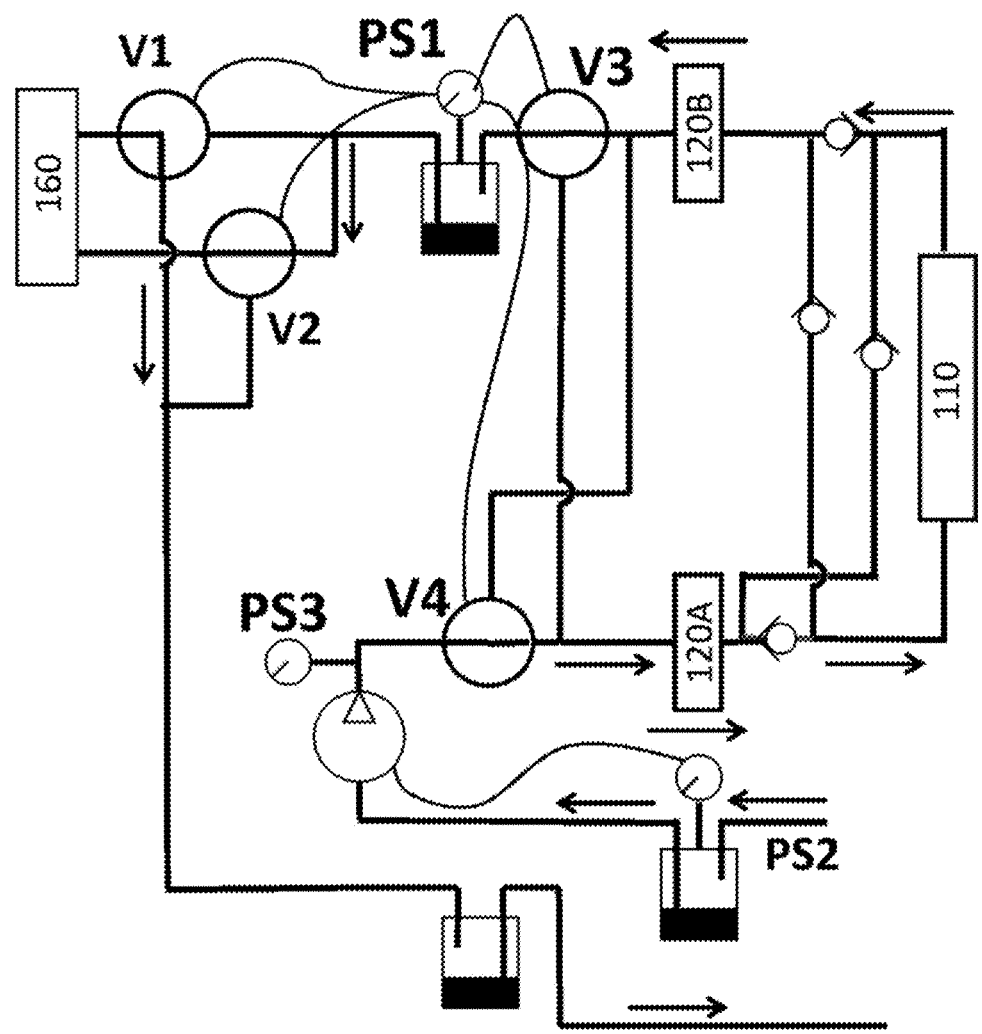
FIG. 6A is a schematic showing the dialysate regenerator in accordance with some embodiments of the disclosure in a first state ST1.
Figure 6B:
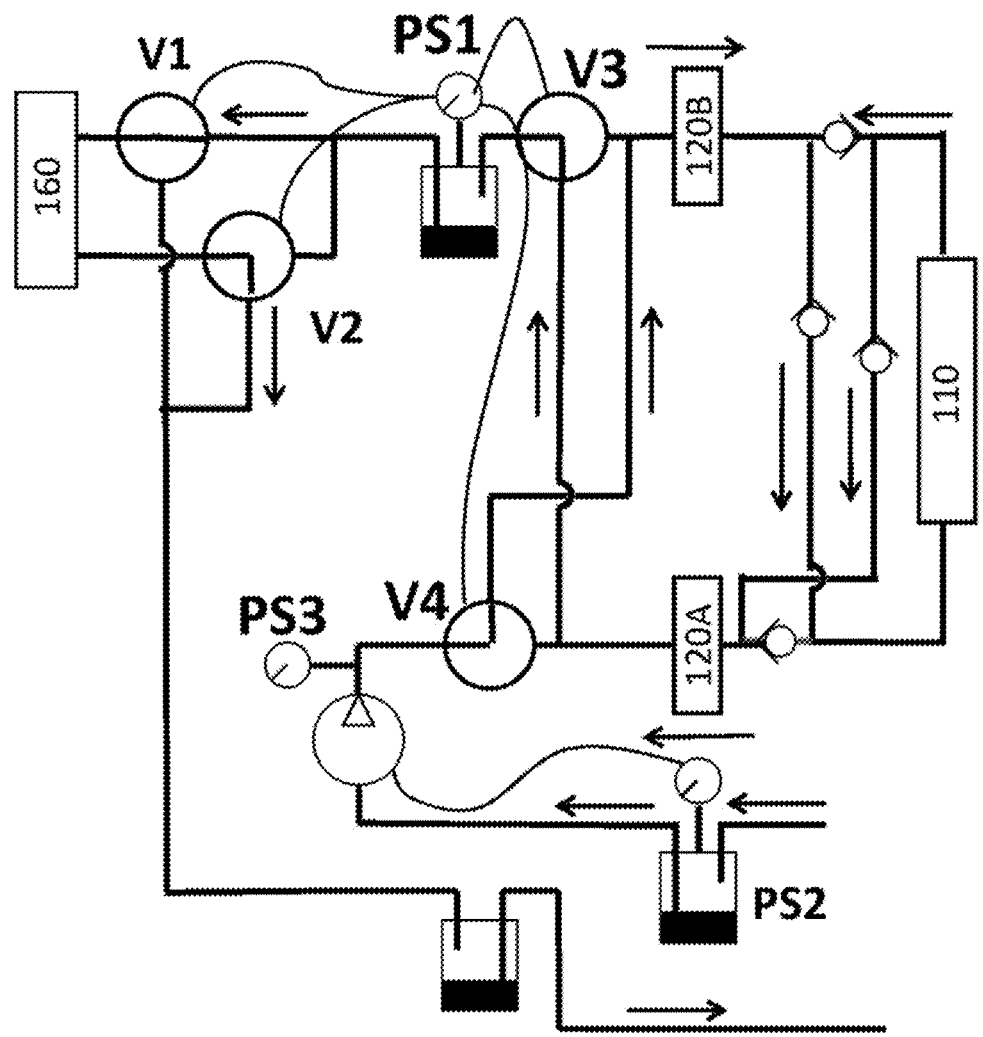
FIG. 6B is a schematic showing the dialysate regenerator in accordance with some embodiments of the disclosure in a first state ST2.
Figure 6C:
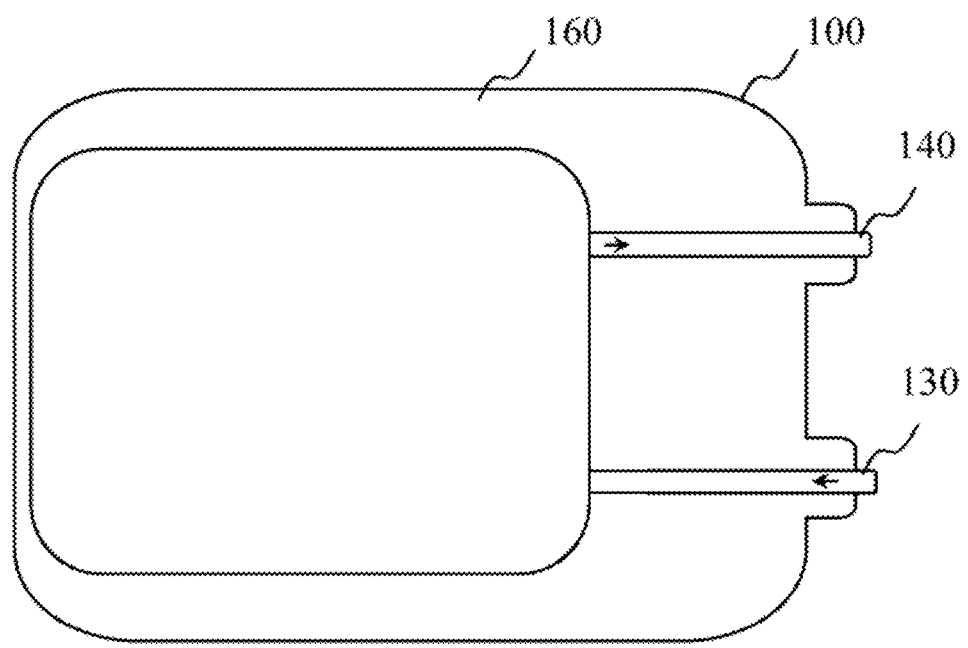
FIG. 6C is a schematic of a fluid portioning system.

In the embodiment shown in FIG. 6A and FIG. 6B, the dialysate regenerator 100 may additionally include one or more valves. The valves may include two sets of inverting valve arrangements. In particular, one or more valves, or one set of valves, may alternate the direction of the dialysate flow path direction through the reversible retainer 120 between a first direction and a second direction, the second direction being reverse to the first direction. A further one or more, or one set of valves, may alternate the direction of the dialysate flow path direction between the fluid portioning system 160 and the dialysate outlet 140 for dispensing the dialysate.

According to some embodiments, the dialysate regenerator 100 may additionally include one or more pressure sensors. The one or more pressure sensor may detect the external pressure at the volume control means 115, for example the pressure sensor may include the pressure sensor PS1 illustrated in FIG. 6A and FIG. 6B. One of the pressure sensors, e.g. PS2, may be positioned in the dialysis flow path upstream of the purification means 110. This sensor may be used to detect a change of pressure or dialysate flow entering the dialysate inlet, and to regulate a pump accordingly. Another of the pressure sensors may be positioned in the dialysis flow path between purification means and fluid portioning system. The two sets of inverting valve arrangements may be synchronised and triggered by detection of a pressure increase at this pressure sensor. In another embodiment, the pressure sensor, for example, pressure sensor PS2, may be positioned downstream of the fluid portioning system. This sensor may be used to detect a change of pressure or dialysate flow withdrawn from the dialysate outlet, and to regulate a pump accordingly.

Figure 7:
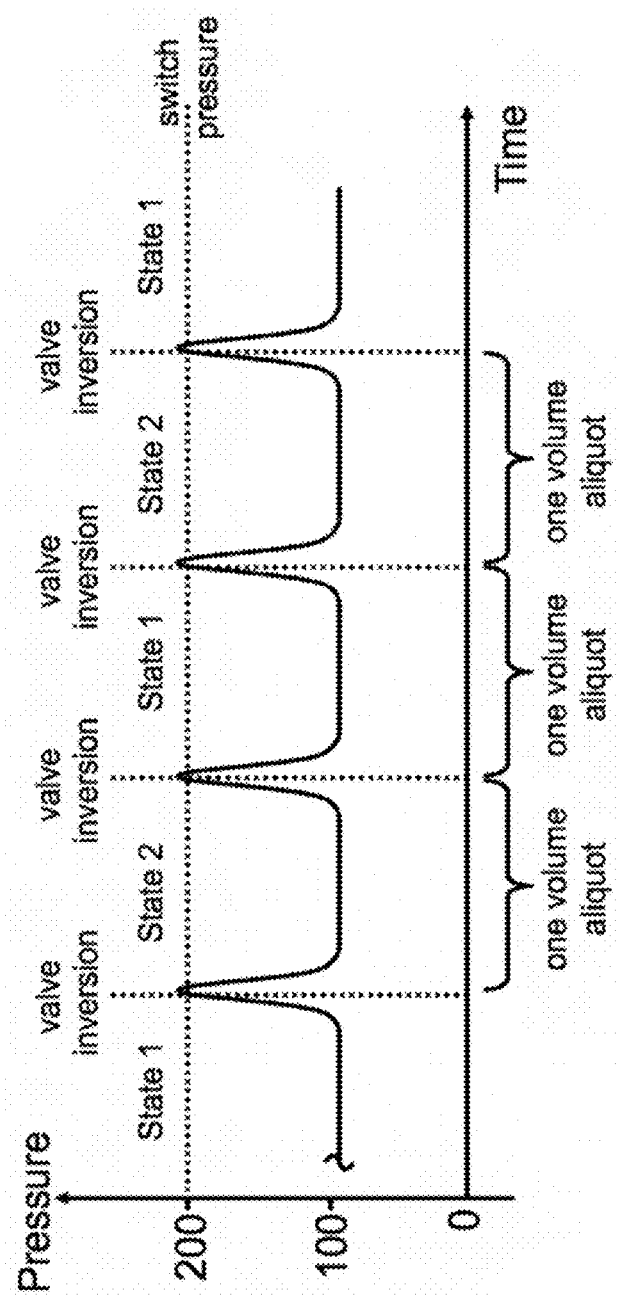
FIG. 7 is an illustration of the valve control principle with idealized pressure reading at PS1.

According to some embodiments, the purification means 110 may be connected to the dialysate flow path in such a way that it only receives dialysate which has previously passed through one of the reversible retainers 120A or 120B, while releasing dialysate through the other reversible retainers 120A or 120B. FIG. 6A and FIG. 6B illustrate an embodiment wherein the valves are connected to the pressure sensor 170 (PS1) and the fluid portioning system. With each detection of a pressure increase at a pressure sensor PS1 (see FIG. 6B, FIG. 7), the system inverts the flow direction through V1/V2 and V3/V4. The flow conduit system is thereby arranged in such a way that the dialysate flow direction through the purification means 110 is never changed, while the dialysate flow direction through the reversible retainers 120A or 120B is regularly inverted, after equal portions of dialysate are defined by the portioning system.

Referring to the first state (ST1) in FIG. 6A, spent dialysate originating from a connected dialysis machine, e.g. a HD machine, is guided through V4 to reversible retainer 120A, where essential ions are temporarily bound. The pre-filtered, toxin-laden dialysate is then de-toxified in the purification means 110. Regenerated dialysate leaving the purification means 110 is passed through reversible retainer 120B, thereby back-washing this reversible retainer, and releasing previously bound essential ions into the regenerated dialysate. The thus reconstituted dialysate is passed through V3 and V2 to a first compartment of a fluid portioning system. At the same time, an equivalent volume of previously regenerated and reconstituted dialysate is released from a second compartment of the fluid portioning system 160 through V1, and is delivered to the HD machine as fresh dialysate. Once PS1 detects that the first compartment of the fluid portioning system 160 is filled completely, all valves are switched synchronously and the system is transferred to ST2 depicted in FIG. 6B.

In the second state (ST2) in FIG. 6B, the spent dialysate drained from the HD machine is passed through V4 to reversible retainer 120B, the reversible retainer which was previously backwashed in ST1. Reversible retainer 120B adsorbs all essential ions from spent dialysate prior to its de-toxification in the purification means 110. The de-toxified dialysate exiting the purification means 110 is guided to back-wash reversible retainer 120A and to release all essential ions bound in the previous ST1. The thus reconstituted dialysate flows through V3 and V1 into the second compartment of the fluid portioning system, releasing the equivalent volume of regenerated dialysate from the first compartment of the fluid portioning system 160 to the HD machine. As soon as PS1 detects that the second compartment of the fluid portioning system 160 is filled (see FIG. 6A, FIG. 7), all valves are switched again and the system is returned to ST1.

The repeated alternation between ST1 and ST2 at regular volume intervals determined by the fluid portioning system 160 results in a continuous regeneration and reconstitution of dialysate (compare with FIG. 5A and FIG. 5B).

As described above in context with the pump and according to some embodiments, the dialysate regenerator 100 may include a temporary storage volume 180. In one embodiment the temporary storage 180 volume is located upstream of said purification means 110. The function of the temporary storage volume is to accommodate the tidal volume. In some embodiments, it may also be used as a portioning system, and/or as a pump.

According to some embodiments, the dialysate regenerator 100 may include sensing means, or a substance sensor. The sensing means may be configured to detect potentially harmful conditions in the regenerated dialysate. Such potentially harmful conditions may include excessive concentrations of ammonia or potassium in regenerated dialysate. Due to the presence of the sensing means, the electronic control of the dialysate regenerator will be able to detect an alarm condition and produce appropriate steps such as stopping the therapy and/or alerting the user.

According to some embodiments, the dialysate regenerator 100 may include control electronics. The control electronics may be configured to control the operation of said dialysate regenerator 100. There may also be provided an interface means capable of operably coupling the control electronics and the dialysate regenerator 100 to enable the removal of toxins from the dialysate. The dialysate flow path may be fluidly sealed from the control electronics and interface means.

The at least one reversible retainer 120 including the ion reservoir may be part of a disposable system, or could even become a non-disposable permanent component of a dialysate regenerator 100. As it is continuously regenerated, the ion reservoir in the reversible retainer 120 would not be expected to exhaust. On the contrary, re-use of a reversible retainer 120 including the ion reservoir may be of advantage for a continuous dialysis therapy, as this will eliminate the stabilisation period (as described further above).

Embodiments described in the context of the dialysate regenerator 100 are analogously valid for the context of the dialysis device. Similarly, embodiments described in the context of the dialysate regenerator 100 are analogously valid for a medical use of the dialysate regenerator 100, and vice-versa.

In a second aspect, there is provided use of an ion reservoir in the manufacture of a dialysate regenerator 100 including said ion reservoir included in at least one reversible retainer 120 for the treatment of a patient suffering from renal insufficiency, liver failure or respiratory insufficiencies with abnormally high levels of one or more toxins or insufficient removal of metabolic waste products or $CO_2$, said treatment including moving a dialysate of the patient through a dialysate flow path including a dialysate inlet 130 for receiving a dialysate by action of a pump, a dialysate outlet for dispensing the dialysate, and a purification means 110, wherein a flow of the dialysate is generated from the dialysate inlet via the reversible retainer 120 and the purification means 110 to the dialysate outlet 140, wherein a direction of the dialysate flow path through the reversible retainer 120 is reversible.

In a third aspect, there is provided a dialysis device 200 including the dialysate regenerator 100 as described above.

In a fourth aspect, there is provided a dialysate regenerator 100 as described above for use in therapy.

In a fifth aspect, there is provided a method of treating a patient suffering from renal insufficiency, liver failure or respiratory insufficiencies with abnormally high levels of one or more toxins or insufficient removal of metabolic waste products or $CO_2$, the method including moving a dialysate of the patient through a dialysate flow path including a dialysate inlet 130 for receiving a dialysate by action of a pump 150, a dialysate outlet 140 for dispensing the dialysate, and a purification means 110, wherein a flow of the dialysate is generated from the dialysate inlet 130 via a reversible retainer 120 including an ion reservoir and the purification means to the dialysate outlet 140, wherein a direction of the dialysate flow path through the reversible retainer 120 is reversible.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

By "about" in relation to a given numerical value, such as for weight percentage (wt %), temperature and period of time, it is meant to include numerical values within 10% of the specified value.

As used herein, the term "and/or" includes any and all combinations of one or more of the associated listed items.

EXAMPLES

Some embodiments of this disclosure are directed to substantially quantitatively adsorb and desorb calcium and magnesium ions on a reversible retainer 120, which may be termed "pre-filter" in the present section.

Advantageously, the ion exchanger used herein may exert a weak binding attraction to Ca and Mg ions. It may be, for example, a weakly acidic cation exchanger. The cation exchanger may have an acid dissociation constant (pKa) in the range of 3 to 10, or optionally in that range of the pH value of the dialysate, i.e. close to physiological range (pKa 5-8). The ion exchanger may be in the form of particles, granules, beads, fabric or membranes. For example, hydrous zirconium oxide is a granular material that has weak cation exchange properties (besides its anion exchange properties) in the desired range.

The pre-filter may have sufficient binding capacity to adsorb the desired amount of Ca and Mg ions contained in the volume of dialysate pumped during each flow mode. Its capacity may be chosen such that excess amounts of Ca and Mg are deliberately "overflowing" the pre-filter into the main sorbent, where they will be adsorbed. The physical dimension of the filter can thereby still remain quite small. For example, a total of 250 ml dialysate may be moved in each flow mode. This volume then contains only a combined total of approximately 0.35 mmol of Ca and Mg. This requires at most a few grams of a typical ion exchanger material, and may for example be achieved by a single layer of an ion exchange fabric pad, or an ion exchange membrane.

The pre-filter may quantitatively (or substantially quantitatively) release the bound cations upon backwashing with regenerated dialysate. This may be effected by the changed ion concentration of Ca and Mg in regenerated dialysate. The sorbent regeneration of dialysate also produces typical pH fluctuations, which can be exploited to support the Ca and Mg adsorption and desorption process. Dialysate returning from the sorbent has generally a slightly lower pH (approximately 6.5-7.2) than dialysate coming from the patient (approximately 7.4). The exchange of Ca and Mg for H and Na in the pre-filter already lowers the pH of the spent dialysate entering the sorbent system. The dialysate exiting the sorbent has a formally increased $pCO_2$, resulting in a further slight decrease of pH. This lower pH facilitates the reversed exchange of H and Na against Ca and Mg in the pre-filter. At the same time, the dialysate's pH is slightly increased and moves closer to the physiological target of 7.4.

Example 1

Figure 8:
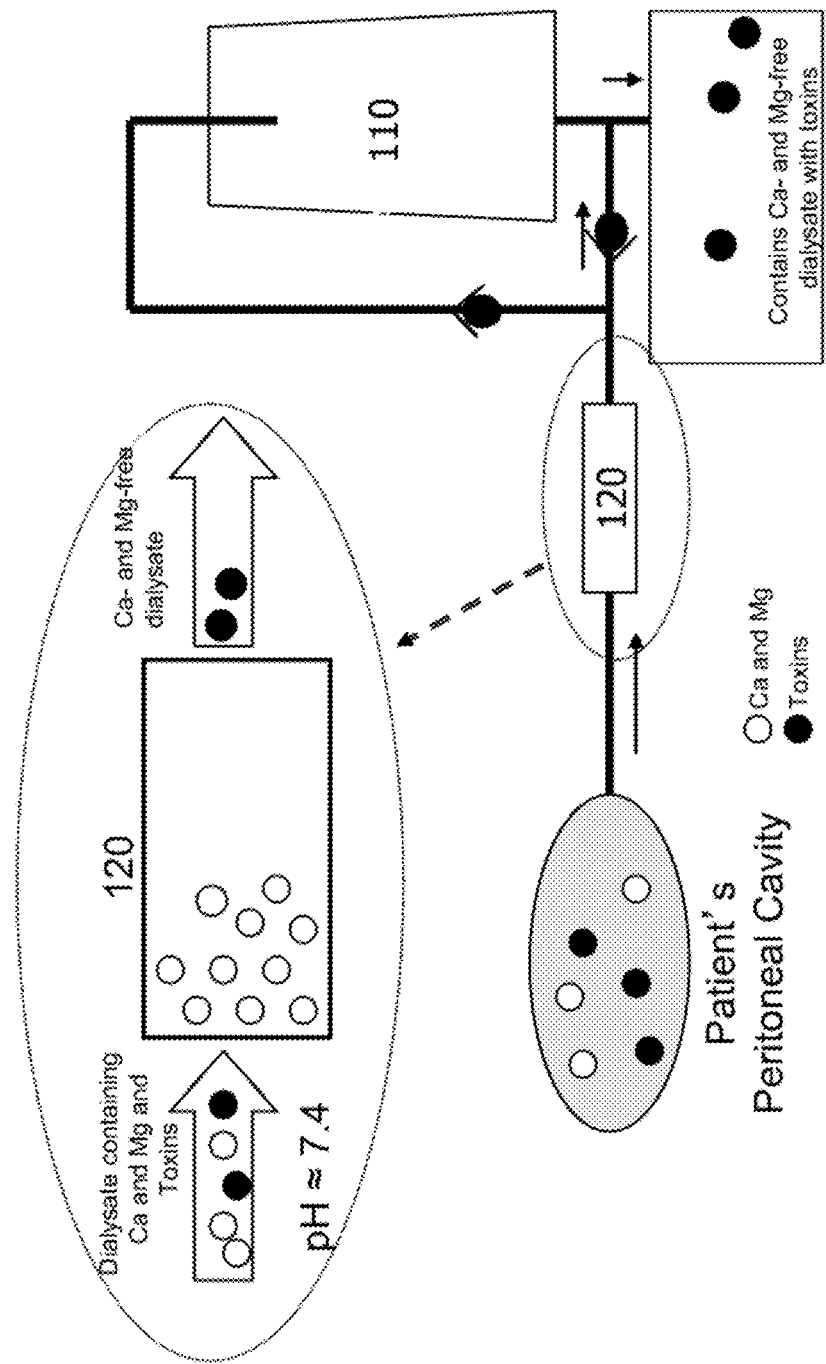
FIG. 8 is an illustration of the flow of spent dialysate through the reversible retainer.
Figure 9:
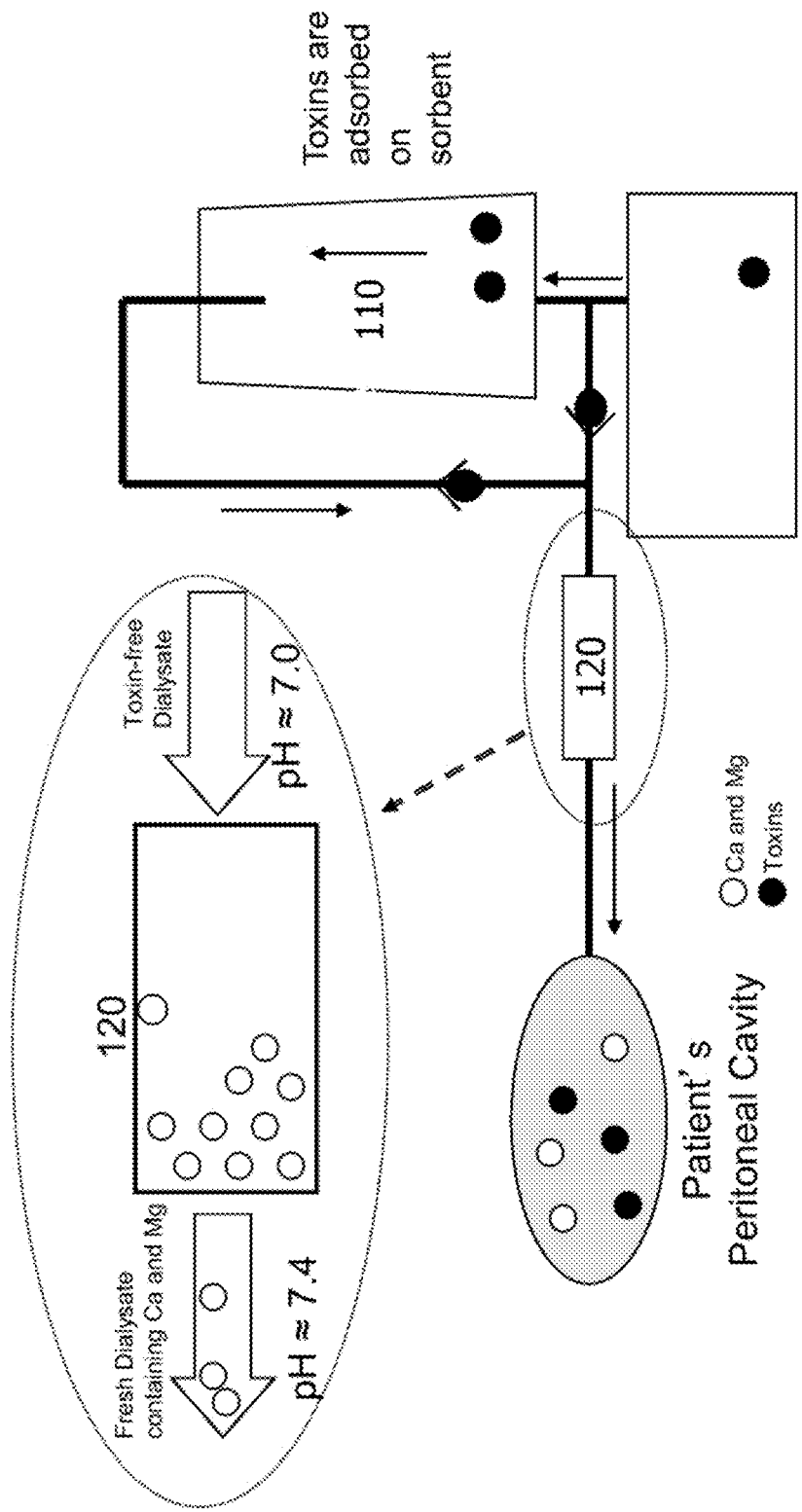
FIG. 9 is an illustration of the flow of regenerated dialysate through the reversible retainer.

FIG. 8 and FIG. 9 show a schematic diagram for a possible arrangement of pre-filter, temporary storage volume and purification means in a proposed dialysate regenerator for a tidal peritoneal dialysis machine.

During a first flow phase ("Outflow", FIG. 8), spent toxin laden dialysate is withdrawn from the patient. Appropriate pump action and check-valve configuration sucks the dialysate through the pre-filter into the temporary storage volume. All Ca and Mg is retained in the pre-filter, which thereby gets saturated in Ca and Mg. The dialysate collected in the temporary storage volume is free of Ca and Mg, but still contains Na, Cl, $HCO_3$, K and uremic toxins most notably urea, creatinine and phosphate.

In the second flow phase ("Inflow", FIG. 9), the dialysate is pressed out of the temporary storage volume and through the sorbent system where uremic toxins and K are adsorbed to >90%. The toxin-free dialysate leaving the sorbent system is essentially free of uremic toxins, and contains almost exclusively Na, Cl and $HCO_3$ ions. The check-valves in the flow circuit then serve to guide this solution through the pre-filter, in opposite flow direction as in the "Outflow" phase. In doing so, all bound Ca and Mg is exchanged by H and Na and re-dissolved into the dialysate. The dialysate returning to the patient thus has the same amount of Ca and Mg as the dialysate that was withdrawn from the patient.

Figure 2:
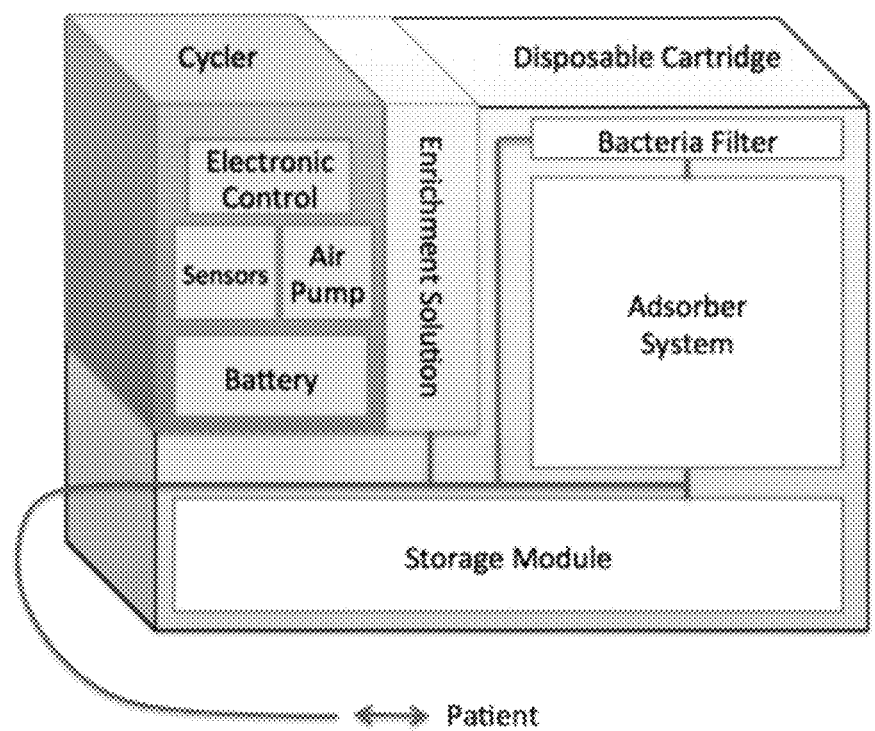
FIG. 2 shows a setup of a conventional sorbent-based peritoneal dialysis device.
Figure 3:
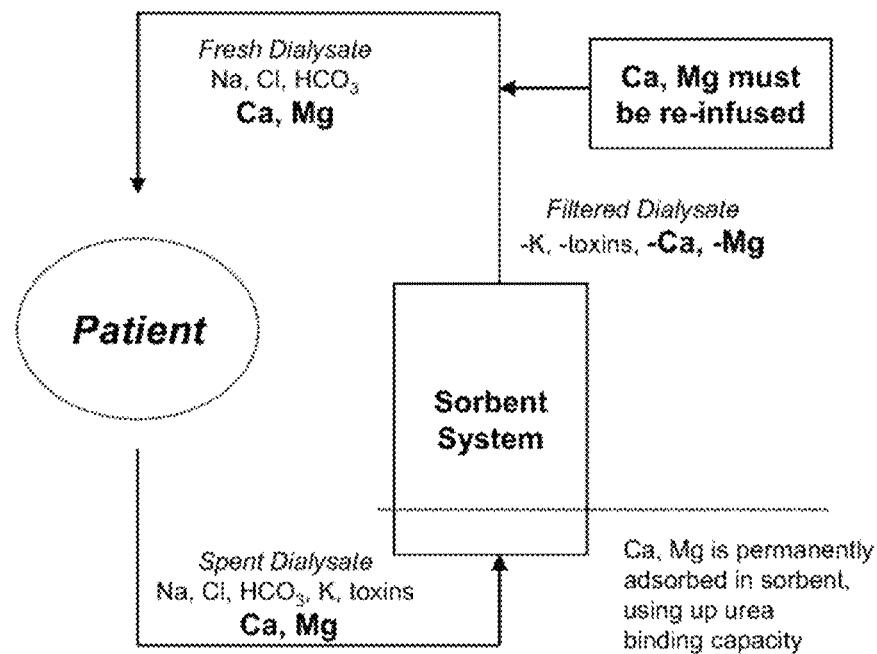
FIG. 3 is a schematic illustrating the basic elements of a conventional sorbent regeneration process.
Figure 10:
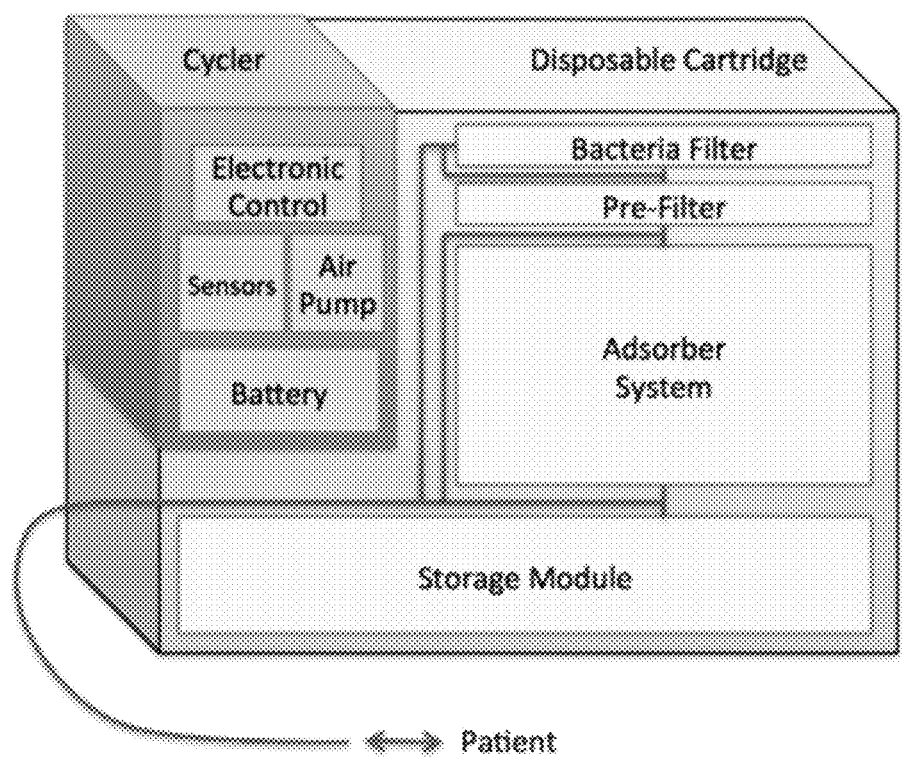
FIG. 10 is an illustration of the integration of the reversible retainer.

FIG. 2 shows a conventional sorbent-based PD system. FIG. 10 depicts a proposed modification of the existing design to implement a pre-filter. The main changes are one additional flow channel and two additional check-valves to ensure correct flow directions in the two flow phases. As the infusate system becomes obsolete, it may be removed and the sorbent system may be expanded accordingly.

If desired, a smaller version of the infusate system may be maintained to infuse a concentrated solution of an osmotic agent such as e.g. a commercial glucose solution. Most importantly, and in contrast to the electrolyte re-infusion, the infusion of osmotic agent may be regulated independently of the main dialysate pumping rate. This opens the possibility of a future sensor-regulated control of the osmotic pressure of the dialysate.

The requirement for electrolyte re-infusion is a major drawback of existing sorbent-based dialysate regeneration systems. It is cumbersome to use and complicated to implement, poses a potential safety risk, and it increases the size and cost of disposables.

The unnecessary adsorption of Ca and Mg means wasted urea adsorption capacity, and the concurrent increase in Na concentration, and/or acidification of the regenerated dialysate is undesirable. Electrolyte solutions for infusion in Peritoneal Dialysis (PD) machines must be sterile, and the machine design must ensure that sterility is maintained during connection and use.

Lastly, concerning PD, the infusion of a thus far unregistered electrolyte solution to regenerated peritoneal dialysate leads to regulatory complications and the classification of the PD sorbent system as a combination of a medical device and an unregistered drug.

The objective of this disclosure is to find a way to re-use established and proven-to-be-safe sorbent technology, while eliminating the requirement for electrolyte re-infusion. The new approach should simplify existing designs, eliminate regulatory obstacles and provide a safe pathway for new, cost efficient miniaturised devices.

This disclosure aims to provide a new technique for selective and efficient sorbent dialysate regeneration without the requirement for electrolyte re-infusion. This is achieved by reversible binding of essential electrolytes on a suitable pre-filter material, such as an ion exchanger. Calcium and magnesium-free dialysate is then regenerated on a conventional sorbent system. The pre-filter is washed back with regenerated dialysate, dissolving the retained electrolytes in the process, and effectively re-constituting the dialysate to its initial electrolyte concentration.

The new approach has the potential to provide significant design simplifications of disposable components of sorbent dialysis machines. It allows the development of miniaturized self-care dialysis machines of high marketing potential, increasing patient comfort, safety and efficacy of treatment at a lower cost than existing devices.

Material Screening. Several groups of materials have been tested for their suitability for use as pre-filter material. Powdered materials were packed into customised plastic cartridges constructed from two joined 10 mL or 20 mL plastic syringes. The length of the cartridges could be customised according to the desired amount of ion exchanger it should contain. For example, an approximately 3 cm long cartridge constructed from 10 mL syringes could hold approximately 3 g of ZP or HZO, but only 1.5 g of the resin-based ion exchangers.

Alternatively, a miniature glass column ("flex column") was packed with ion exchanger, and the layer was tightly compressed with cotton. In yet another embodiment, a re-usable cylindrical ø40 mm prototype cartridge was packed with a 5-10 mm layer of ion exchanger. Membrane ion exchangers were fixed in a re-usable 24 mm diameter disk membrane holder.

Figure 11:
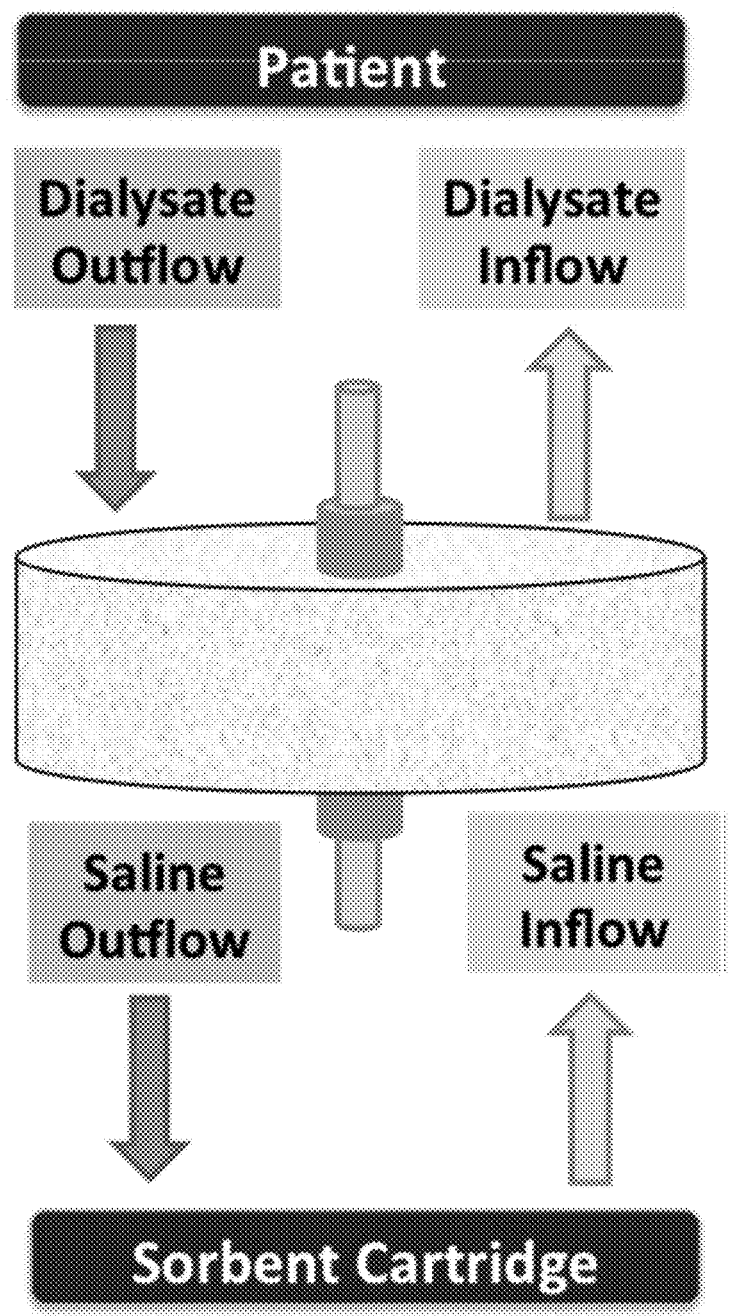
FIG. 11 is an illustration of the a test setup.

All test cartridges were used in both flow directions (see, FIG. 11). First, an idealised "dialysate outflow" solution was passed through the test cartridge in one direction, and Ca and Mg was quantified in the fluid exiting the cartridge ("saline outflow"). Then the cartridge was turned around, and the same volume of idealised "saline inflow" solution (simulating toxin-free dialysate leaving the sorbent system) was passed through the cartridge in opposite direction. The fluid exiting the cartridge in this direction ("dialysate inflow") was again assayed for Ca and Mg.

Such cycles were repeated at least 20 times to see if observed effects—if any—were repeatable. The idealised outflow solution was a bicarbonate buffered dialysate solution at pH 7.5, containing no toxins and no glucose. The idealised inflow solution was a solution of only NaCl and $NaHCO_3$ at pH 6.3 to 6.5. A suitable pre-filter material would have been characterised by approximately quantitative adsorption of Ca and Mg from the "dialysate outflow", and approximately quantitative recovery of Ca and Mg in the "dialysate inflow". Beyond that, factors like binding capacity and flow resistance were taken into account.

The volume of dialysate which could be regenerated, and the mass of ion exchanger that was contained in such a miniature cartridge was used to extrapolate the required mass for use in a sorbent-based peritoneal dialysis device.

Figure 12:
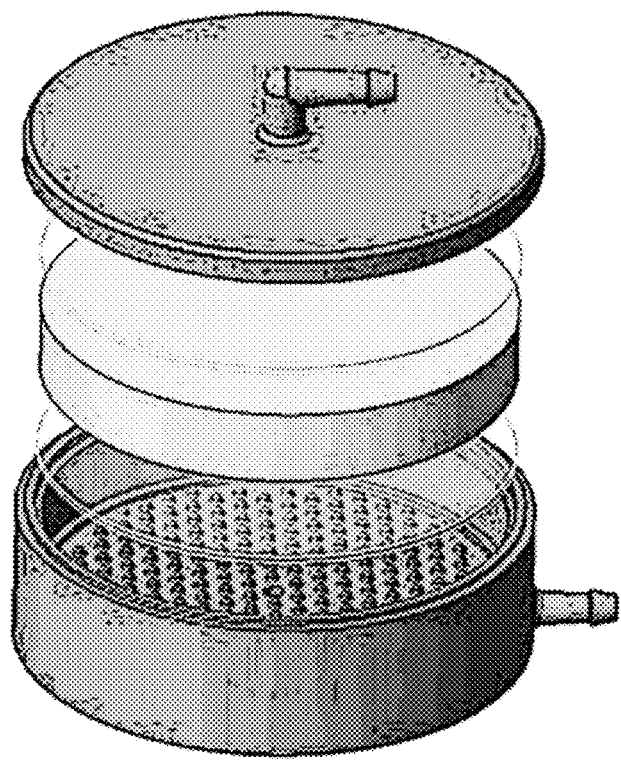
FIG. 12 is an illustration of the cylindrical full-size reversible retainer prototype.

Off-line tests. The following test step involved full-size prototypes containing the calculated quantity of ion exchanger (see, FIG. 12). To this end, cylindrical single-use prototypes were printed using a 3D printer. The prototypes were designed such that their height could easily be increased or reduced as required. If necessary, printed cylindrical spacers could be inserted to reduce the internal volume further.

Figure 13:
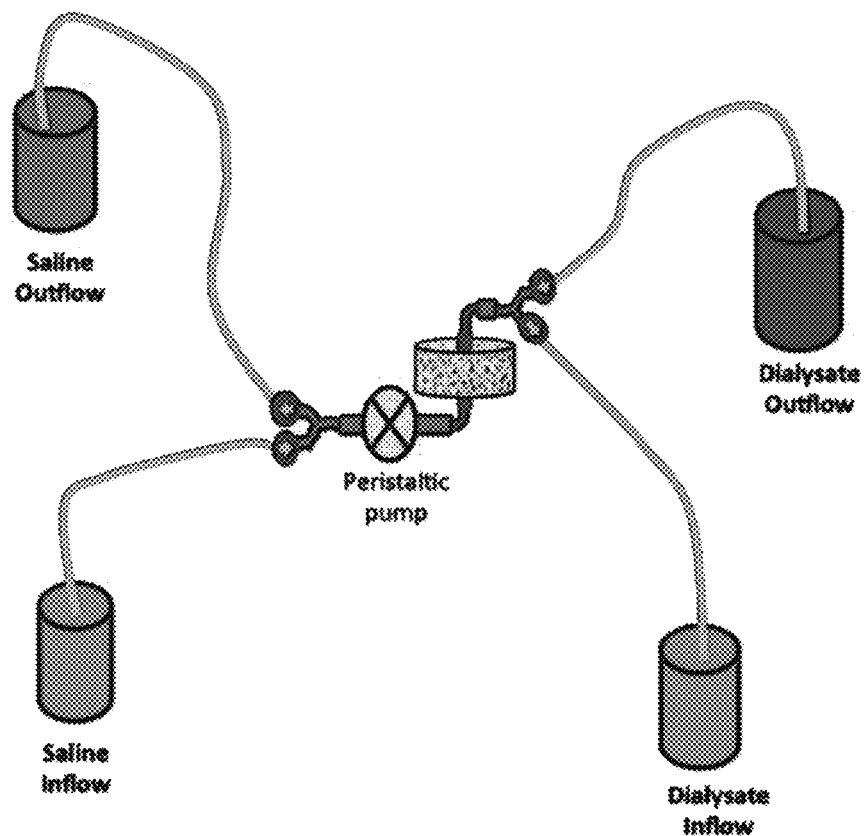
FIG. 13 is an illustration of the In-vitro off-line test setup.

The cylindrical prototypes were then tested in-vitro as shown in FIG. 13, with a simulated tidal volume of 275 mL of "dialysate outflow" and "saline inflow" for at least 20 cycles, using a bi-directional peristaltic pump.

In-line tests. Once the pre-filter dimensions had been optimised in off-line tests, the filters were tested in combination with a conventional sorbent cartridge, without electrolyte re-infusion. Simulated patient spent dialysate containing toxins and glucose was used as "dialysate outflow". The regenerated dialysate after the conventional purification means was directed back to the pre-filter, replacing the "saline inflow" of the offline tests. Finally, the fluid exiting the pre-filter was tested as "dialysate inflow" and the Ca and Mg recovery was assessed.

Figure 14:
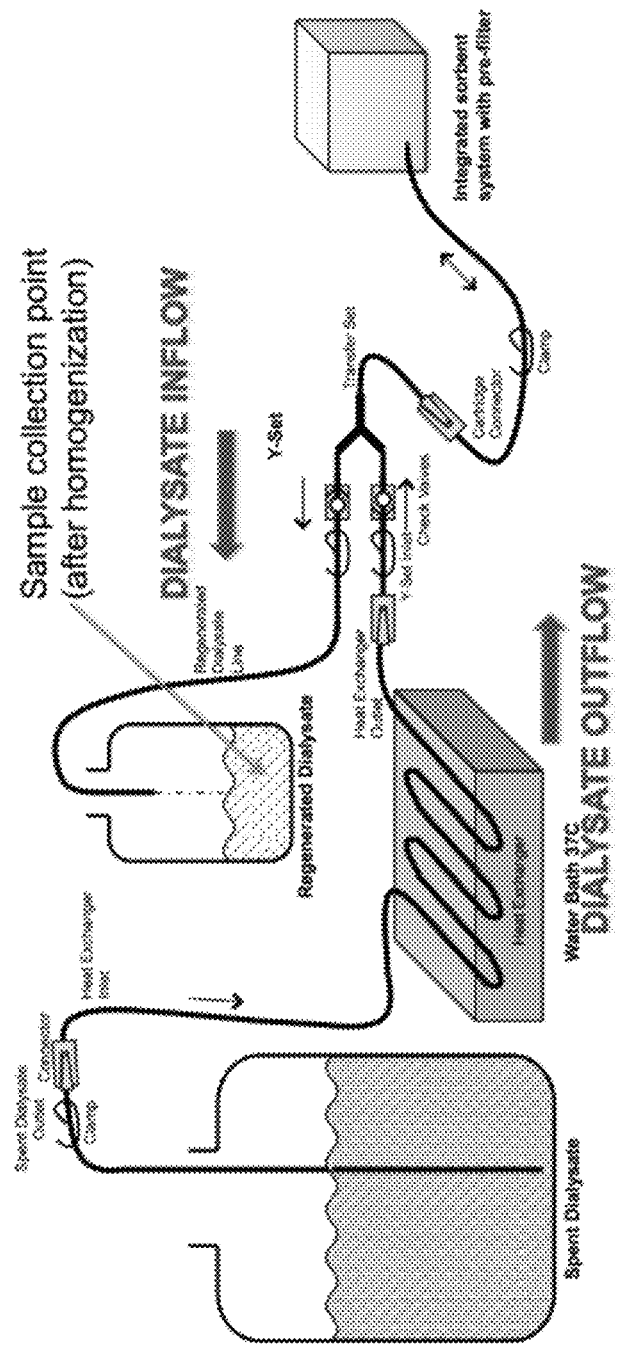
FIG. 14 is an illustration of the Integrated system test setup.

Tests with integrated prototypes. Integrated system tests were performed with different versions of integrated designs. Some of which were tested on partial component level, others were done with full prototypes using the new designs (see, FIG. 14). Those tests primarily served for mechanical evaluation of the design, and for in-vitro evaluation of the performance.

Prototyping. Early prototypes were produced by stereolithography (SLA) or machining. Subsequent prototypes were generated using a Stratasys EDEN 260V 3D printer. Using this 3D printer, watertight prototypes of high accuracy and mechanical strength were developed.

Example 2: Results and Discussion

Selection of Preferred Pre-Filter Material. Table 1 shows a summary of the obtained screening results with a selection of different ion exchange materials. It should be noted that only a limited number of materials was used, and that other materials within the tested categories may be found which may perform differently. The assessment of suitability should therefore only be interpreted for the particular material samples tested, and not for entire material categories.

TABLE 1

Material screening results

| Material | Removal Efficiency | Recovery Efficiency | Comment |
| --- | --- | --- | --- |
| Zirconium Phosphate | High | Low | Not suitable |
| Organic resin ion exchangers | Low | Medium | Not suitable |
| Modified Activated Carbon | Low | Medium | Not suitable |
| Ion Exchange Membranes | High | High | Costly |
| Hydrous Zirconium Oxide | Medium | High | High Resistance Suitable |

Zirconium Phosphate. Zirconium Phosphate was an obvious candidate to be tested in this study, being the cation exchanger used in the current conventional sorbent systems. Its cation exchange properties are based on interactions with phosphate groups at a wide pH range spanning from pH2-pH8. Its performance as pre-filter material was not satisfactory, however. This is believed to be due to its significantly higher affinity to Ca and Mg, relative to Na and H, possibly due to complex formation. In other words, H was unable to dislodge Ca and Mg from its binding sites to any significant amount. The resulting retention rates for Ca and Mg were too low to be useful for pre-filter application.

Carboxylic acid based ion exchangers. The majority of weakly acidic cation exchangers rely on the action of carboxylic acid functional groups, which bind to H or other cations. Their pK of 3-5 means that the typical pH fluctuations in dialysate regeneration would effect significant changes in the protonation grade of the material, which is an essential requirement for reversible ion exchange in this study.

The resin-based cation exchangers tested in this study fall into this group, as well as oxidised activated carbon and oxycellulose. All those materials showed similarly unsatisfactory Ca and Mg retention rates. This may again be due to complex formation with bivalent cations, translating into a significantly higher affinity to Ca and Mg, relative to Na and H.

Ion exchange membranes. The tested ion exchange membranes had reasonably high binding capacity and recovery efficiency. However, their high flow resistance and high material cost were a serious drawback for their application in a disposable cartridge.

Hydrous Zirconium Oxides. Hydrous zirconium oxide is generally considered an anion exchanger, which exchanges hydroxide or acetate against other anions, such as e.g. phosphate or fluoride. However, it has also cation exchange properties, which became apparent during material tests, where not only the actual target, phosphate, was removed, but unexpectedly also Ca and Mg. The assumed mechanisms for anion and cation exchange are depicted in Scheme 1. Thus, while anion exchange involves the dissociation of Zr—O bonds, cation exchange involves the dissociation of ZrO—H bonds.

Material screening tests have revealed that HZO indeed has suitable properties for the objectives of this study. A difference of 1 pH unit was sufficient for complete adsorption of Ca and Mg at high pH, and complete desorption at low pH. The material offered the added advantage of being part of conventional sorbent systems, such that its biocompatibility is well established. The use of the same type of material for main sorbent and pre-filter is also expected to facilitate regulatory processes. This made HZO the material of choice.

However, three issues needed to be addressed:
  quantitative recovery of Ca and Mg was only achieved after several cycles of adsorption and desorption;
  the Na loading and cation exchange capacity was not perfect;
  the flow resistance was slightly high.

Efforts were made to overcome these shortcomings by appropriate modification of HZO.

Optimisation of material properties. Two types of HZO were available, following two different production methods ("Type 1" and "Type 2"). One of these had superior capacity for Ca and Mg at better retention rates and was thus preferred.

Figure 15:
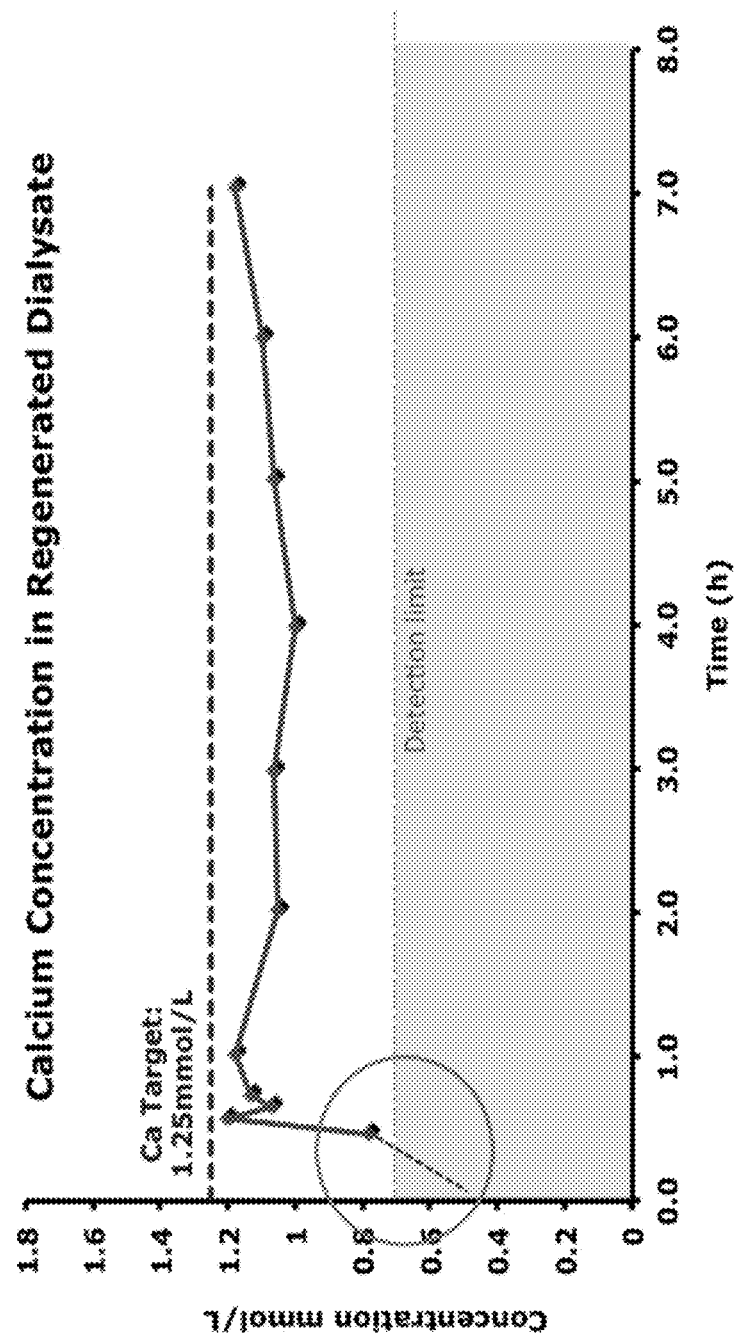
FIG. 15 is a graph showing the typical in-vitro behaviour of reversible retainer without pre-conditioning.
Figure 16:
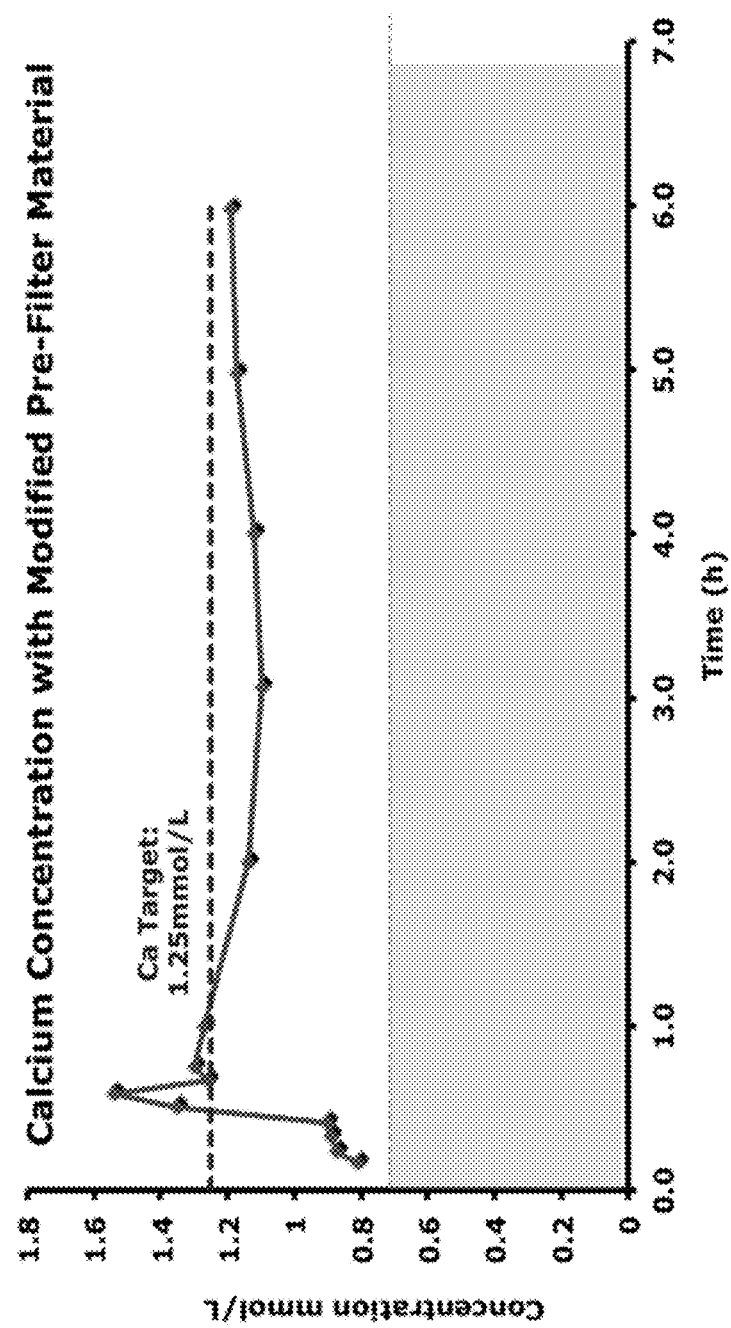
FIG. 16 is a graph showing the similar reversible retainer as in FIG. 15, after first pre-conditioning attempts.

Pre-treatment and drying. One of the key challenges for optimisation was the tendency of the pre-filter material to undergo gradual changes during use, which usually meant that Ca and Mg retention rates were low at the beginning of the experiments and only reached satisfactory levels after lengthy periods of stabilisation (see, FIG. 15). This problem was eventually overcome by finding appropriate procedures for pre-conditioning HZO with solutions of Ca and Mg salts (see, FIG. 16). The optimised conditions for pre-treatment were found empirically by iterative modification of concentrations, duration, number of repetitions, and number of washing steps. The result was a pre-filter, which provided stable Ca and Mg retention rates right from the start of the experiments—see, Table 2. A suitable procedure was, for example, to condition 400 g of HZO in a solution of 2.28 g NaCl, 1.18 g NaHCO$_3$ 6.98 g CaCl$_2$ and 0.44 g MgCl$_2$ at room temperature, followed by filtration and air drying at 40 C.

TABLE 2 is a Table showing the reversible retainer performance after optimised preconditioning conditions for 5 g Pre-Treated Type I, 250 mL

| Set 1 | Ca | Mg | K | Phos |
|---|---|---|---|---|
| D0 | 1.28 | 0.30 | 2.0 | 1.02 |
| D1-D4 | 1.36 | 0.30 | 0.4 | 0.52 |
| D5-D8 | 1.21 | 0.30 | 0.4 | 0.65 |
| D9-D12 | 1.21 | 0.30 | 0.4 | 0.66 |
| D13-D16 | 1.22 | 0.30 | 0.4 | 0.64 |
| D17-D20 | 1.13 | 0.28 | 0.4 | 0.70 |
| Recovery | 99 | 99 | | |
| Removal | | | 80 | 38 |

Sieving. The materials' flow resistance was influenced by material washing, pre-treatment and drying. However, the best effect was achieved by sieving the material after drying. Thus, sieving and selecting a desired particle size range (e.g. 50-100 µm) gave the lowest pressure drop and fastest achievable dialysate flow rates.

HZO filter pad. The investigation of HZO filter pads was done in an attempt to get away from a fixed particle bed, to a pre-filter containing HZO fixed on a 3 dimensional scaffold (filter pad). The flow resistance of such filter pads is primarily determined by the structure of the cellulose support. Filter pads do also have significant advantages for ease of assembly. A suitable filter pad manufacturing procedure was, for example, to mix 5.6 g of filter paper (small pieces) and 37.56 g of HZO in a solution of 2.87 g NaCl, 1.49 g NaHCO$_3$ 14.37 g CaCl$_2$) and 1.06 g MgCl$_2$. This mixture was mechanically stirred until a homogenous mash was obtained. Then, 1.40 g dextrin, 0.06 g starch, 0.37 g sodium carboxymethyl cellulose and 0.01 g sodium benzoate was added. Casting and drying provided 4 HZO filter pads.

Optimisation of pre-filter size. The next step of development involved the optimisation of pre-filter capacity and dimensions. This was done with component-level prototypes, which were either run off-line using idealised dialysate solutions, or in-line in conjunction with conventional sorbent cartridges. In an initial phase, it was attempted to attain complete retention of the desired target concentrations of Ca and Mg, while removing any excess. In the course of these efforts, it became clear that the pre-filters also had a tendency for partial adsorption of K and phosphate during outflow, which were then equally desorbed during inflow, resulting in a partial retention of those undesired components. Larger sized pre-filters provided increased Ca and Mg retention rates, but also reduced K and phosphate removal rates (for example 80 g, see, Table 3).

TABLE 3 is a Table showing the IV performance of a large size reversible retainer, 80 g Pre-Treated Type I, 250 mL

| Set 6 | Ca | Mg | K | Phos |
|---|---|---|---|---|
| D0 | 1.23 | 0.25 | 2.0 | 1.00 |
| D1-D4 | 0.91 | 0.17 | 1.9 | 0.37 |
| D5-D8 | 0.95 | 0.17 | 1.8 | 0.53 |
| D9-D12 | 0.99 | 0.18 | 1.9 | 0.66 |
| D13-D16 | 1.09 | 0.21 | 1.9 | 0.76 |
| D17-D20 | 1.18 | 0.21 | 1.9 | 0.86 |
| Recovery | 83 | 75 | | |
| Removal | | | 6 | 36 |

Smaller filters improved the K and phosphate removal, sometimes to an undesirably high level of K removal. Adjustment of the pre-treatment conditions, and reduction of the pre-filter size improved the performance further (see, Table 4, Table 5).

TABLE 4

Table showing the IV performance of a small size reversible retainer, 10 g Pre-Treated Type I, 250 mL

| Set 2 | Ca | Mg | K | Phos |
|---|---|---|---|---|
| D0 | 1.34 | 0.24 | 2.0 | 1.03 |
| D1-D4 | 1.12 | 0.19 | 0.8 | 0.44 |
| D5-D8 | 1.20 | 0.22 | 0.7 | 0.60 |
| D9-D12 | 1.36 | 0.25 | 0.8 | 0.75 |
| D13-D16 | 1.29 | 0.23 | 0.8 | 0.80 |
| D17-D20 | 1.26 | 0.22 | 0.7 | 0.86 |
| Recovery | 93 | 93 | | |
| Removal | | | 62 | 33 |

TABLE 5 is a Table showing the optimised reversible retainer size IV performance, 10 g Type I, 250 mL

| Set 5 | Ca | Mg | K | Phos |
|---|---|---|---|---|
| D0 | 1.24 | 0.25 | 2.0 | 1.23 |
| D1-D4 | 1.16 | 0.20 | 0.6 | 0.64 |
| D5-D8 | 1.17 | 0.21 | 0.7 | 0.74 |
| D9-D12 | 1.25 | 0.25 | 0.7 | 0.80 |
| D13-D16 | 1.23 | 0.21 | 0.7 | 0.80 |
| D17-D20 | 1.28 | 0.24 | 0.7 | 0.92 |
| Recovery | 97 | 87 | | |
| Removal | | | 66 | 37 |

Attempts to reduce the K and phosphate retention (i.e. increase the removal rate) by pre-saturation with K and phosphate solution were unsuccessful. The final optimisation result is a compromise between both factors, where the pre-filter retains approximately 90% of the target Ca and Mg, while allowing approximately 60-70% of K and 30-40% of phosphate to pass through and be removed by the main sorbent (see, Table 5). A suitable pre-filter for a dialysate volume of 250 mL had, for example, a diameter of 70 mm and contained approx. 12 g of HZO.

Example 3: In-Vitro Tests

Off-line experiments. The off-line experiments used idealised settings for the simulation of expected conditions. The predictive value of these experiments is limited by the absence of toxins and proteins in the outflow solution, and the choice of pH and Na concentration in the inflow solution. Further, the assumption of constant composition of outflow and inflow solutions neglected the possibility of gradual concentration changes over the intended therapy timespan. However, those experiments have proven extremely useful for high level screening of materials as well as the initial material optimisation steps.

In vitro tests. The bulk of the optimisation work was done on component-level tests using a modular setup of actual sized pre-filter prototypes and conventional sorbent cartridge prototypes. The best results were obtained with a cylindrical prototype pre-filter of 70 mm diameter for an outflow/inflow volume of 250 mL. When combined with a conventional sorbent cartridge, this pre-filter provided an average retention of 97% and 87% for Ca and Mg, respectively, while allowing for 66% of K and 37% of phosphate to be removed (see, Table 5). The filter also performed favourably under simulated extreme conditions of high Ca, high Mg and high K. Similar results were also obtained with HZO Type II, as shown in FIG. 17 and FIG. 18. As intended, excess Ca in outflow was readily removed such that the inflow Ca concentration met the target criteria. Hence, the pre-filter was able to correct the effects of a simulated hypercalcaemia. The situation was slightly different for excess Mg, where the surplus of Mg was partially retained while Ca was slightly reduced. The absolute effect was comparatively low, as the concentration of Mg was only approximately ⅕ of that of Ca. The total amount of retained K appeared to be constant, even at different outflow K concentrations. As a result, higher K concentrations led to higher K removal rates. The situation is similar for phosphate. Phosphate, too, was only retained until a certain level, and any further amount was removed. The incomplete removal of K and phosphate is considered advantageous, as high volume dialysis with dialysate containing no K and phosphate may result in hypokalaemia and hypophosphataemia. The partial retention of those two components might therefore be desired.

Example 4: Embodiment with at Least Two Reversible Retainers

All test cartridges were used in both flow directions (see, FIG. 11). First, an idealised "dialysate outflow" solution was passed through the test cartridge in one direction, Ca and Mg was detectable in the fluid exiting the cartridge ("saline outflow"). Then the cartridge was turned around, and the same volume of idealised "saline inflow" solution was passed through in opposite direction. The fluid exiting the cartridge in this direction ("dialysate inflow") was again assayed for Ca and Mg.

The idealised outflow solution was a bicarbonate buffered dialysate solution at pH 7.3 to 7.5, containing no toxins and no glucose. The idealised inflow solution was a solution of only NaCl and NaHCO$_3$ at pH 6.3 to 6.5. Desired material properties were approximately quantitative adsorption of Ca and Mg from the "dialysate outflow", and approximately quantitative recovery of Ca and Mg in the "dialysate inflow". Beyond that, other factors like flow resistance were taken into account.

The 3D printed prototypes were then tested in-vitro as shown in FIG. 13, with a simulated portioning volume of 300 mL of "dialysate outflow" and "saline inflow" for at least 20 cycles, using a bi-directional peristaltic pump.

Initial efforts focused on the screening of different types of HZO sorbent material (see, Table 6). A preferred material was identified showing greater than 70% electrolyte recovery and good potassium and phosphate removal under standardized test conditions. 81.7% Ca and 72.9% Mg were recovered, and 52.6% K and 76.10% PO$_4$ were removed when compared to the initial concentration of the dialysate solution.

TABLE 6

Different types of HZO sorbent material and their removal qualities

| FORMULATION SUMMARY | PFS005-063A | PFS005-069B | PFS005-069C | PFS005-069D | PFS005-117 |
|---|---|---|---|---|---|
| Calcium % Recovery | 74.5 | 71.4 | 62.5 | 69 | 81.7 |
| Magnesium % Recovery | 106.5 | 128.2 | 90.7 | 107 | 72.9 |
| Potassium % Removal | 18.5 | 21.1 | 48.2 | 59.1 | 52.6 |
| Phosphate % Removal | 68.2 | 62.9 | 81.8 | 82 | 76.1 |

Full system integration/integrated cartridge design. The optimized pre-filter dimensions were then integrated in the design of a fully integrated disposable cartridge.

Figure 23:
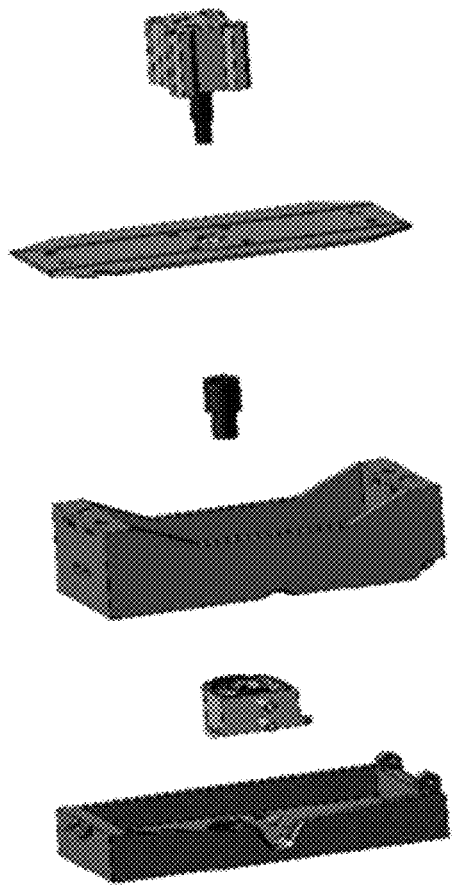
FIG. 23 shows a Single Cylinder test setup to determine optimum air pressure setting in a pneumatic cylinder.
Figure 24:
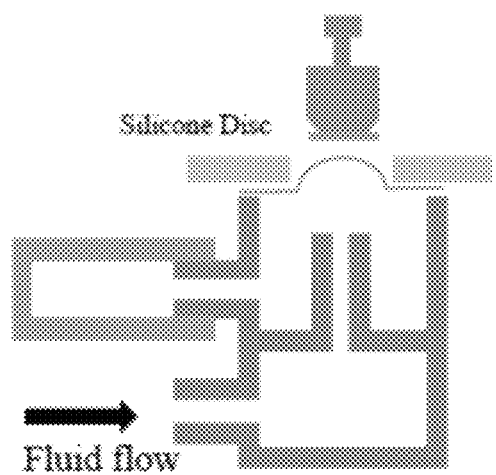
FIG. 24 shows a Single Cylinder test setup to determine optimum air pressure setting in pneumatic cylinder.

Hydraulic circuit valve design (V1, V2, V3 and V4). Each direction control valve (V1, V2, V3 and V4) in the integrated cartridge consisted of a rigid flow chamber, which was sealed by a flexible PVC membrane on one side (see, FIG. 23 and FIG. 24). The flow chamber had a fluid inlet channel and a fluid outlet channel. The inlet channel was located in close proximity to the flexible PVC membrane, such that pressing the flexible membrane onto the inlet channel opening could seal the channel. The pressing was done with the help of pneumatic cylinders (one for each valve), which were equipped with silicone plungers. The valves were thus naturally open 2/2 valves, which could be closed by activating the pneumatic plungers. The optimum pressure setting for the pneumatic cylinder was determined for different fluid pressures and silicone plunger diameters.

The preferred pneumatic cylinder was CJ2B6 from SMC as the size was deemed suitable in the whole integration design. The diameter of the valve inlet channel was 3 mm (Inner Diameter) and 6 mm (Outer Diameter). The test results are shown in the Table 7 below.

TABLE 7

| Full system test/validation | | |
|---|---|---|
| Silicone Disc Diameter (φ8 mm) | | |
| Fluid flow pressure | 0.6 bar | 1.0 bar |
| Cylinder pressure | 2.0 bar | 3.2 bar |
| Silicone Disc Diameter (φ7 mm) | | |
| Fluid flow pressure | 0.6 bar | 1.0 bar |
| Cylinder pressure | 1.8 bar | 2.8 bar |

For the system test and validation, a component equivalent of the Integrated Prototype was used. Simulated dialysate concentrations included normal, low and high set concentrations for Ca, Mg, K and Phosphate. Calcium recoveries at various concentrations were found to be >80%. Magnesium recoveries were observed to be >70%. Removal of Potassium and Phosphate was found at 48-63% (K) and 28-50% (PO$_4$) respectively. It was also noted that at low Calcium concentration, the recovery was >100%, i.e. there was a slight release of Ca from the (pre-treated) pre-filter.

TABLE 8

Summary of Infusate-free sorbent system performance at various concentration ranges

| Summary | Ca | Recovery | Mg | Recovery | K | Removal | Phos | Removal |
|---|---|---|---|---|---|---|---|---|
| Standard Range | 1.28 | 87% | 0.20 | 76% | 2.01 | 52% | 1.13 | 41% |
| High Potassium | 1.34 | 84% | 0.39 | 71% | 3.87 | 63% | 1.10 | 50% |
| E. High Potassium | 1.28 | 98% | 0.33 | 95% | 5.75 | 58% | 1.18 | 28% |
| Low Phosphate | 1.26 | 89% | 0.31 | 81% | 1.97 | 54% | 0.49 | 34% |
| High Phosphate | 1.25 | 89% | 0.32 | 81% | 2.04 | 48% | 2.37 | 38% |
| Low Calcium | 0.65 | 109% | 0.28 | 99% | 1.96 | 52% | 0.91 | 31% |
| High Calcium | 1.78 | 83% | 0.27 | 71% | 2.04 | 51% | 1.11 | 35% |
| High Magnesium | 1.31 | 95% | 0.86 | 79% | 2.09 | 54% | 1.14 | 33% |

Figure 19A:
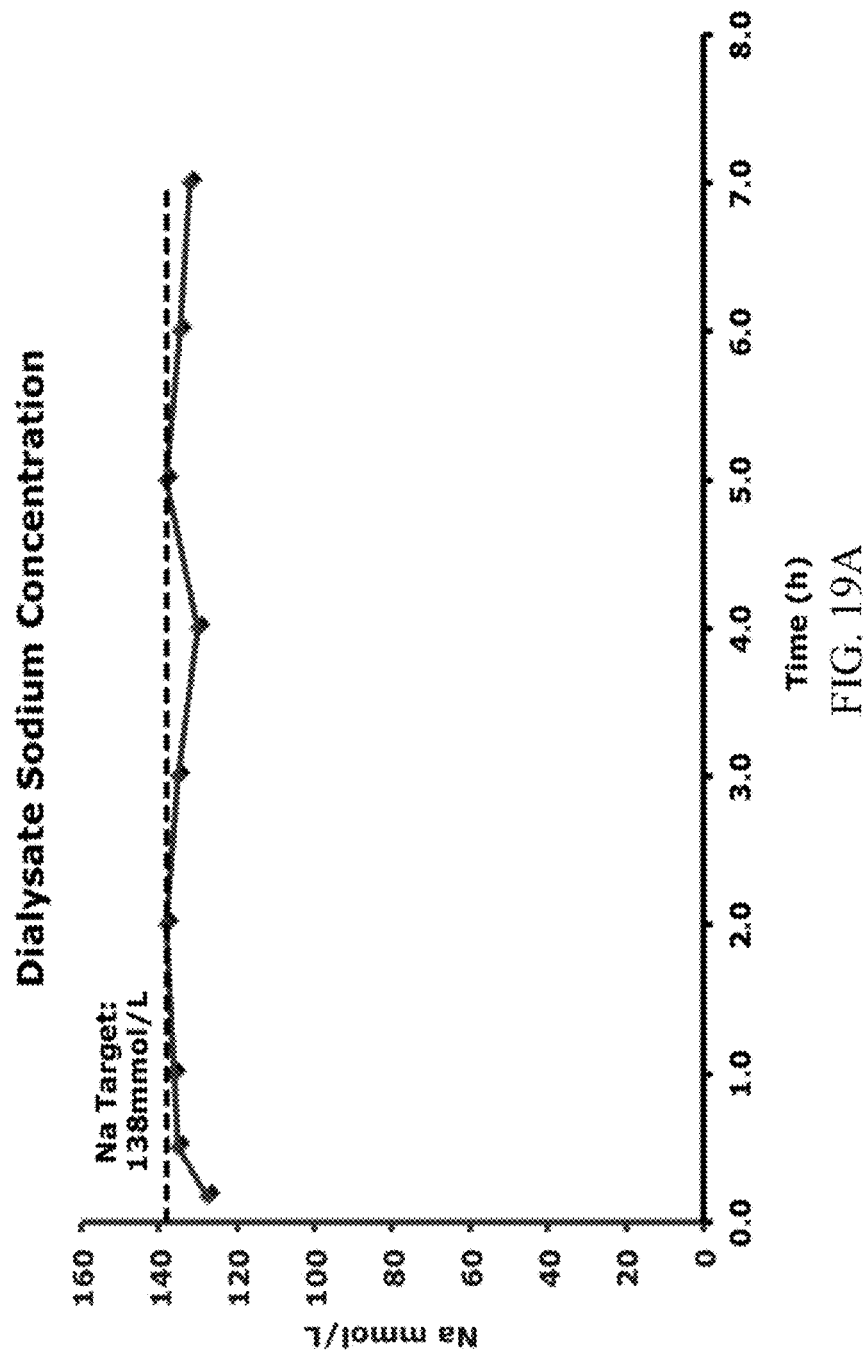
FIG. 19A is a graph showing the sodium concentration in the dialysate in the HD model for an in vitro test.
Figure 19B:
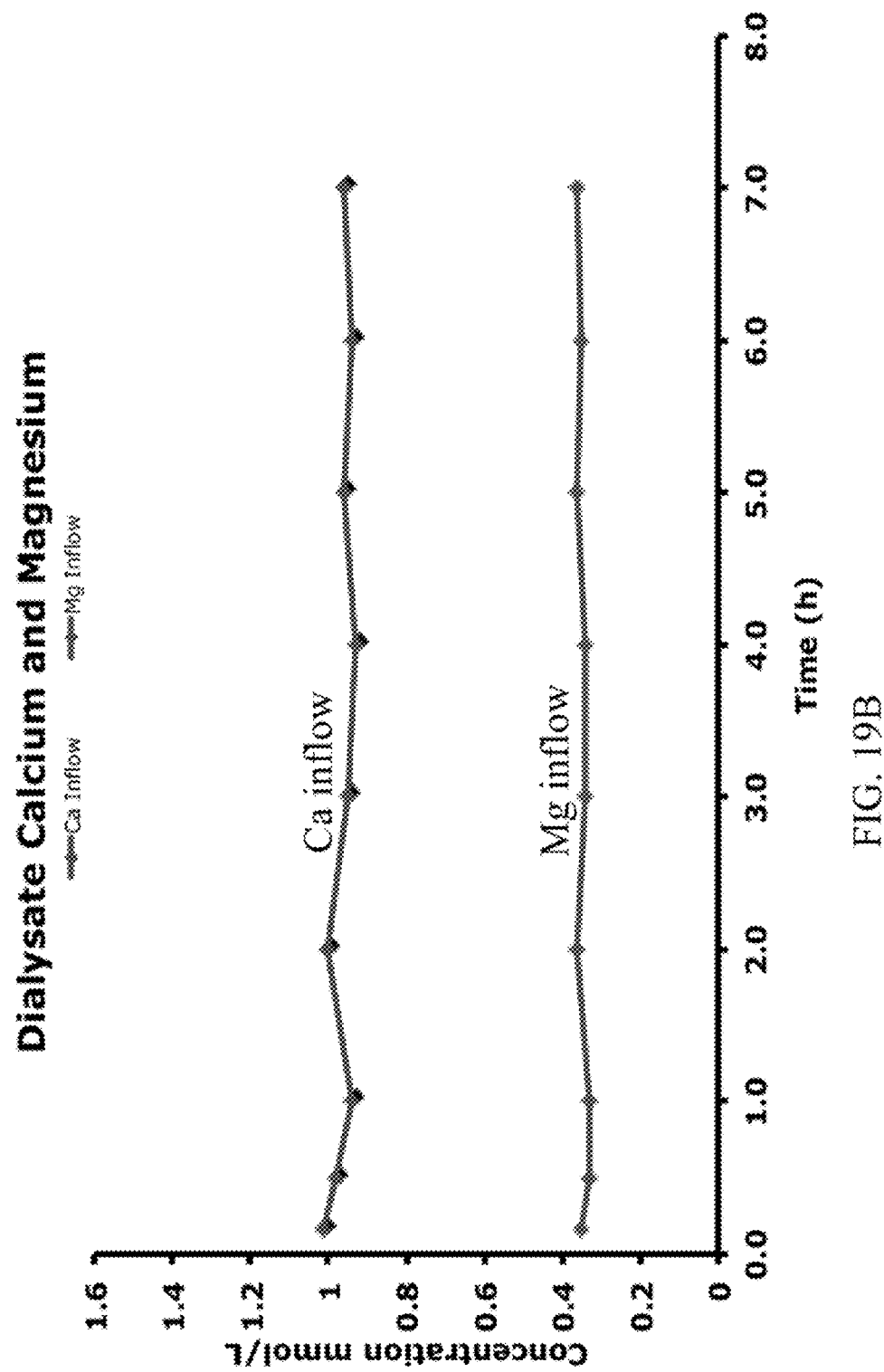
FIG. 19B is a graph showing the calcium and magnesium concentration in the HD model for an in vitro test.
Figure 19C:
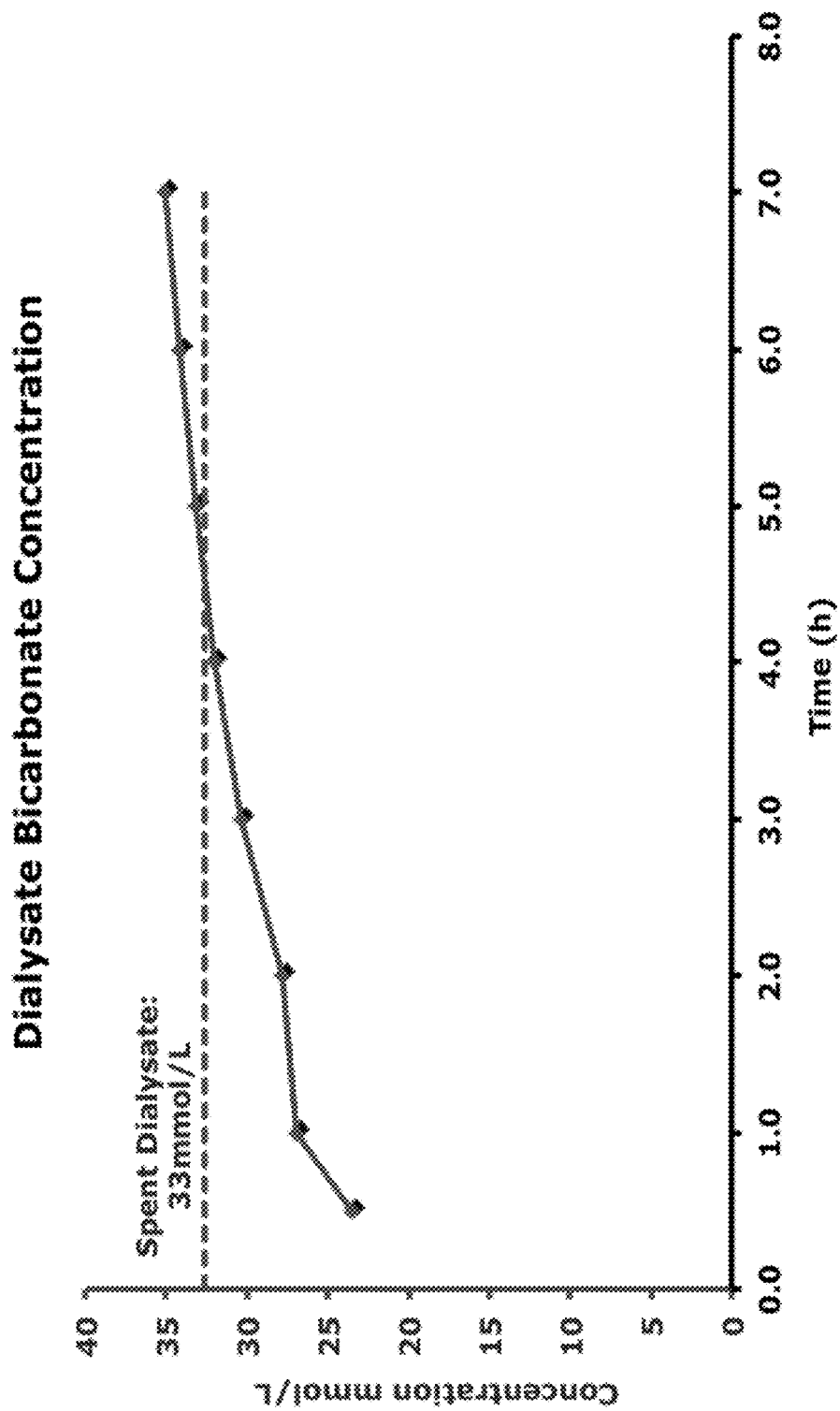
FIG. 19C is a graph showing the bicarbonate concentration in the HD model for an in vitro test, wherein it is shown that the initial reduction of bicarbonate is tunable, hence, if desired, the bicarbonate profile can be flattened and/or offset to higher dialysate bicarbonate concentration.
Figure 20:
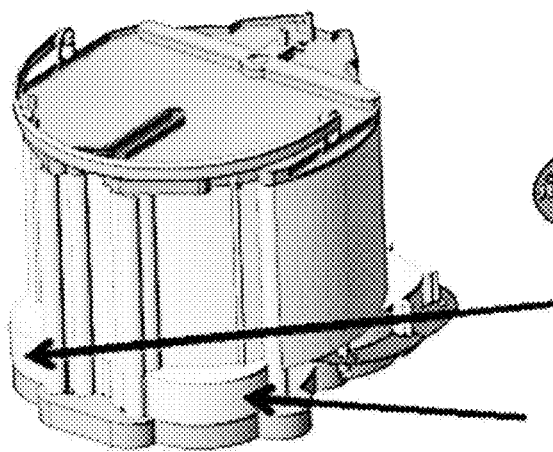
FIG. 20 is an illustration of a schematic model (Top View) of an Integrated prototype UDRS with Infusate-free sorbent.
Figure 21:
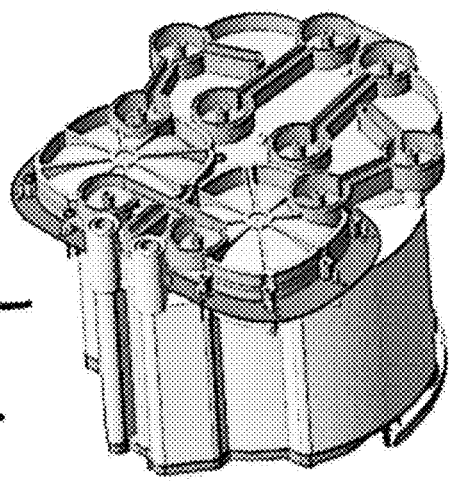
FIG. 21 is an illustration of a schematic model (Bottom view) of an Integrated prototype UDRS with Infusate-free sorbent.
Figure 22:
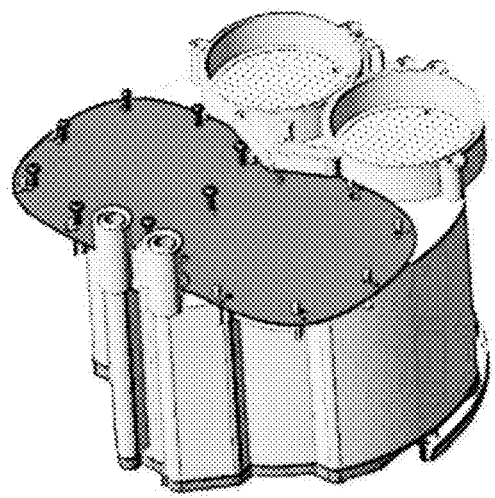
FIG. 22 is an illustration of a schematic model without cover (Bottom view) of an Integrated prototype UDRS with Infusate-free sorbent.

Another full system test was performed on a component level, simulating conditions of a slow, low-flow hemodialysis at a dialysate flow rate of 170 mL/min and a total duration of 7 h. The regenerated dialysate sodium, calcium, magnesium and bicarbonate concentrations remained stable in the desired target concentration range, throughout the 7 h experiment (see FIG. 19A, FIG. 19B, FIG. 19C).

While the disclosure has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A dialysate regenerator, comprising:
   A purification means;
   At least one reversible retainer comprising an ion reservoir;
   A dialysate flow path comprising a dialysate inlet for receiving a dialysate, and a dialysate outlet for dispensing the dialysate;
   A plurality of valves for alternating a direction of the dialysate flow path through the at least one reversible retainer between a first direction and a second direction, the second direction being reverse to the first direction; and
   A pump connected to the dialysate flow path and configured to generate a flow of the dialysate from the dialysate inlet via the reversible retainer and the purification means to the dialysate outlet,
   Wherein the at least one reversible retainer is positioned upstream of the purification means in the first direction of the dialysate flow path and positioned downstream of the purification means in the second direction of the dialysate flow path, wherein the second direction of the dialysate flow path through the reversible retainer is reverse to the first direction of the dialysate flow path through the reversible retainer; or
   Wherein the dialysate regenerator comprises a first reversible retainer upstream of the purification means and a second reversible retainer downstream of the purification means.

2. The dialysate regenerator of claim 1, wherein the ion reservoir comprises an ion exchanger.

3. The dialysate regenerator of claim 1, wherein the dialysate regenerator comprises a volume control means configured to direct a predetermined volume of the dialysate from the dialysate inlet via the reversible retainer and the purification means to the dialysate outlet.

4. The dialysate regenerator of claim 2, wherein the ion exchanger is a reversible ion exchanger capable of retaining and releasing ions.

5. The dialysate regenerator of claim 2, wherein the ion exchanger changes from being predominantly an anion exchanger at a pH value of below 5 to predominantly a cation exchanger at a pH value of above 8.

6. The dialysate regenerator of claim 2, wherein the ion exchanger is hydrous zirconium oxide (HZO).

7. The dialysate regenerator of claim 2, wherein the ion exchanger in a pristine state comprises essential ions.

8. The dialysate regenerator of claim 2, wherein the ion exchanger is embedded in a filter pad and/or an additional sorbent bed.

9. The dialysate regenerator of claim 1, wherein the reversible retainer is configured to decrease the pH of a dialysate upstream of the purification means by retaining ions from the dialysate.

10. The dialysate regenerator of claim 1, wherein the reversible retainer is configured to increase the pH of a dialysate downstream of the purification means by releasing ions into the dialysate.

11. The dialysate regenerator of claim 1, wherein the dialysate regenerator comprises a pressure sensor (PS1).

12. The dialysate regenerator of claim 1, wherein the dialysate regenerator comprises one reversible retainer positioned upstream of the purification means in a first direction of the dialysate flow path through the reversible retainer and the same reversible retainer positioned downstream of the purification means in a second direction of the dialysate flow path, wherein the second direction of the dialysate flow path through the reversible retainer is reverse to the first direction of the dialysate flow path through the reversible retainer.

13. The dialysate regenerator of claim 1, wherein the dialysate regenerator comprises a temporary storage volume.

14. The dialysate regenerator of claim 13, wherein the plurality of valves alternate the dialysate flow path between
   A first flow phase from the dialysate inlet to the temporary storage volume via the reversible retainer; and
   A second flow phase from the temporary storage volume to the dialysate outlet via the purification means and the reversible retainer, wherein a direction of the dialysate flow path through the reversible retainer in the second flow phase is reverse to the direction of the dialysate flow path through the reversible retainers in the first flow phase.

15. The dialysate regenerator of claim 1, wherein when the dialysate regenerator comprises a first reversible retainer upstream of the purification means and a second reversible retainer downstream of the purification means, the dialysate regenerator comprises a volume control means configured to direct a predetermined volume of the dialysate from the dialysate inlet via the reversible retainer and the purification means to the dialysate outlet, wherein the volume control means comprises a fluid portioning system to divide a dialysate flow into uniform portions for sequential regeneration.

16. The dialysate regenerator of claim 1, wherein when the dialysate regenerator comprises a first reversible retainer upstream of the purification means and a second reversible retainer downstream of the purification means, the plurality of valves alternate the dialysate flow path between the dialysate inlet and the dialysate outlet in a first state via the reversible retainer, the purification means, and the reversible retainer and in a second state via the reversible retainer, the purification means, and the reversible retainer, wherein a direction of the dialysate flow path through the reversible retainers in the second state is reverse to the direction of the dialysate flow path through the reversible retainers in the first state.

17. The dialysate regenerator of claim 16, wherein the plurality of valves are synchronized and alternate the dialysate flow path between the first and second state upon a pressure change detected by a pressure sensor.

18. The dialysate regenerator of claim 1, wherein the dialysate regenerator comprises a flow adjuster.

19. A dialysis device comprising the dialysate regenerator of claim 1.

\* \* \* \* \*